United States Patent
Hoge et al.

(10) Patent No.: US 8,846,922 B2
(45) Date of Patent: Sep. 30, 2014

(54) FUNCTIONALIZED FLUOROALKYL FLUOROPHOSPHATE SALTS

(75) Inventors: Berthold Theo Hoge, Bielefeld (DE); Anne Julia Bader, Bielefeld (DE); Nikolai Mykola Ignatyev, Duisburg (DE); Michael Schulte, Bischofsheim (DE); Wolfgang Hierse, Gross-Zimmern (DE); Waldemar Wiebe, Cologne (DE); Helge Willner, Muelheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/825,894

(22) PCT Filed: Aug. 30, 2011

(86) PCT No.: PCT/EP2011/004353
§ 371 (c)(1),
(2), (4) Date: Mar. 25, 2013

(87) PCT Pub. No.: WO2012/048772
PCT Pub. Date: Apr. 19, 2012

(65) Prior Publication Data
US 2013/0197228 A1 Aug. 1, 2013

(30) Foreign Application Priority Data

Sep. 27, 2010 (EP) .................... 10010827
Sep. 27, 2010 (EP) .................... 10010828
Sep. 27, 2010 (EP) .................... 10010829

(51) Int. Cl.
| | | |
|---|---|---|
| *C07F 9/6506* | (2006.01) |
| *C07F 9/46* | (2006.01) |
| *C07F 9/58* | (2006.01) |
| *H01M 10/056* | (2010.01) |
| *C07F 9/535* | (2006.01) |
| *C07F 9/54* | (2006.01) |
| *H01M 10/42* | (2006.01) |
| *H01M 10/0567* | (2010.01) |

(52) U.S. Cl.
CPC .............. *C07F 9/6506* (2013.01); *Y02E 60/12* (2013.01); *H01M 10/056* (2013.01); *C07F 9/535* (2013.01); *C07F 9/5442* (2013.01); *C07F 9/58* (2013.01); *H01M 10/4235* (2013.01); *C07F 9/46* (2013.01); *H01M 10/0567* (2013.01); *C07F 9/581* (2013.01)
USPC ............ 546/21; 546/304; 548/335.1; 564/15; 568/14

(58) Field of Classification Search
None
See application file for complete search history.

(56) References Cited

U.S. PATENT DOCUMENTS

| | | | |
|---|---|---|---|
| 6,210,830 B1 | 4/2001 | Sartori et al. |
| 7,094,328 B2 | 8/2006 | Ignatyev et al. |
| 7,153,974 B2 | 12/2006 | Schmidt et al. |
| 8,211,277 B2 | 7/2012 | Ignatyev et al. |
| 2002/0015884 A1 | 2/2002 | Schmidt et al. |
| 2004/0171879 A1 | 9/2004 | Ignatyev et al. |
| 2010/0004461 A1 | 1/2010 | Ignatyev et al. |
| 2012/0264946 A1 | 10/2012 | Ignatyev et al. |

FOREIGN PATENT DOCUMENTS

| | | |
|---|---|---|
| DE | 10 2007 004698 | 8/2008 |
| EP | 0 929 558 | 7/1999 |
| EP | 1 162 204 | 12/2001 |
| WO | WO-02 085919 | 10/2002 |
| WO | WO-03 002579 | 1/2003 |
| WO | WO-2011 072810 | 6/2011 |

OTHER PUBLICATIONS

International Search Report for PCT/EP2011/004353, Date of the actual completion of the international search report: Jan. 16, 2012, Date of mailing of the international search report: Jan. 20, 2012.
Merck Patent GmbH, "Method of producing fluoroalkylphosphates," Espacenet, Publication Date: Oct. 31, 2002; English Abstract of WO-02 085919.
Pavlenko, N. V. et al., "New anions of pentacoordinate phosphorus containing fluorine and trifluoromethyl groups," Eur. J. Inorg. Chem, 2007, pp. 1501-1507.
Pavlenko, N. V. et al., "Reaction of Tris(perfluoroalkyl) phosphine oxides and tris(perfluoroalky) difluorophosphoranes with fluoride ion," Journal of General Chemistry, 1989, vol. 59, No. 3.1, pp. 469-473.

*Primary Examiner* — Janet L Andres
*Assistant Examiner* — Timothy R Rozof
(74) *Attorney, Agent, or Firm* — Millen, White, Zelano & Branigan, P.C.

(57) ABSTRACT

The present invention relates to functionalized fluoroalkylfluorophosphate salts, in particular as ionic liquids, to the preparation thereof and to the use thereof.

15 Claims, No Drawings

FUNCTIONALIZED FLUOROALKYL FLUOROPHOSPHATE SALTS

The present invention relates to functionalised fluoroalkylfluorophosphate salts, in particular as onic liquids, to the preparation thereof and to the use thereof.

Ionic liquids or liquid salts are ionic species which consist of an organic cation and a generally inorganic anion. They do not contain any neutral molecules and usually have melting points below 373 K.

The properties of ionic liquids, for example melting point, thermal and electrochemical stability, viscosity, are strongly influenced by the nature of the anion. On the other hand, the polarity and hydrophilicity or lipophilicity can be varied through a suitable choice of the cation/anion pair. There is therefore a basic demand for novel ionic liquids having varied properties which facilitate additional potential uses.

EP 0 929 558, WO 02/085919 and EP 1 162 204 disclose salts containing perfluoroalkylfluorophosphate anions (FAP anions for short). These salts are distinguished by high electrochemical and thermal stability and at the same time have low viscosity. Salts based on FAP anions are substantially inert and have greater stability to hydrolysis than, for example, salts containing $PF_6^-$ anions.

However, it is often desired to have available compounds, for example as reaction medium, which can be decomposed easily after the reaction has been carried out in order to reduce the environmental pollution with compounds of very low biodegradability.

There is thus a demand for novel compounds which have easier degradability. In the case of organic cations combined with the functionalised fluoroalkylfluorophosphate anions according to the invention, these are particularly preferably ionic liquids.

The object of the present invention is accordingly to provide novel compounds which are suitable, for example, as acid catalyst for chemical reactions, as additive in electrolytes or, in the case of organic cations, as ionic liquids.

The present object is achieved by the compounds according to the invention, processes for the preparation thereof and the use thereof.

The present invention thus relates firstly to compounds of the formula I $$Kt^{Z+}z[P(R_f)_n F_{5-n}X]^- \qquad I,$$

where $R_f$ in each case, independently of one another, denotes a straight-chain or branched fluoroalkyl group having 1 to 8 C atoms,
X denotes OR, Ac, OAr or OHet,
Ac denotes a carboxyl group OC(O)R, also including carboxyl groups of an aliphatic dicarboxylic acid resulting in compounds having the formula Ib

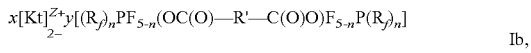

where
x denotes 2 and y denotes 1 if z denotes 1,
x denotes 1 and y denotes 1 if z denotes 2,
x denotes 2 and y denotes 3 if z denotes 3 and
x denotes 1 and y denotes 2 if z denotes 4 and R' denotes a single bond or an alkylene group having 1 to 4 C atoms,
Ar denotes an aryl group having 6 to 12 C atoms, which may be unsubstituted or substituted by Hal, $NH_2$, $NAlk_2$, NHAlk, $NO_2$, CN, $SO_3H$ or OR,
Alk denotes a straight-chain or branched alkyl group having 1 to 12 C atoms,
Het denotes a heteroaryl group having 5 to 13 C atoms, which may be unsubstituted or substituted by Hal, $NH_2$, $NAlk_2$, NHAlk, $NO_2$, CN, $SO_3H$ or OR,
R denotes H or a straight-chain or branched alkyl group having 1 to 20 C atoms, which may be partially substituted by Hal, $NH_2$, NHAlk, $NAlk_2$, OH, $NO_2$, CN or $SO_3H$, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—
and
Kt denotes a stabilised (solvated) proton, a metal cation or an organic cation,
Hal denotes F, Cl, Br or I,
z denotes 1, 2, 3 or 4 and
n denotes 1, 2 or 3, and/or tautomers or stereoisomers thereof, including mixtures thereof in all ratios.

The number z stands for the degree of charging of the cation and thus for the number of anions present in the compounds according to the invention. In total, electroneutrality of the compounds should be ensured. The number z denotes 1, 2, 3 or 4.

The compounds of the formula I according to the invention make it possible to provide ionic liquids having properties which can be adapted to the respective use. The compounds of the formula I are less hydrolytically stable than the perfluoroalkylfluoroposphate anions which are already known and are therefore more easily accessible to biological degradability.

Furthermore, the compounds of the formula I, which tend to be hydrophobic per se, can be converted into the compounds having the same cation, but perfluoroalkylphosphinate anions, which tend to be hydrophilic, by reaction with water or a base. Owing to these unusual properties of the compounds according to the invention, different compounds having certain properties can be prepared as needed, for example for use in extraction methods. In-situ conversion of hydrophobic ionic liquids into hydrophilic ionic liquids enables the development of a simple isolation method of water-insoluble products after a synthesis in hydrophobic ionic liquids of the formula I.

A straight-chain or branched fluoroalkyl group having 1 to 8 C atoms is a partially fluorinated or perfluorinated straight-chain or branched alkyl group having 1 to 8 C atoms, i.e. in the case of a perfluorinated alkyl group all H atoms of this alkyl group have been replaced by F. In the case of a partially fluorinated alkyl group having 1 to 8 C atoms, the alkyl group has at least one F atom, 1, 2, 3 or 4 H atoms are present and the other H atoms of this alkyl group have been replaced by F. Known straight-chain or branched alkyl groups are methyl, ethyl, propyl, isopropyl, n-butyl, sec-butyl, tert-butyl, n-pentyl, n-hexyl, n-heptyl or n-octyl. Preferred examples of the partially fluorinated straight-chain or branched alkyl group $R_f$ are $CF_3$—CHF—$CF_2$—, $CF_2$H—$CF_2$—, $CF_3$—$CF_2$—$CH_2$—, $CF_3$—$CF_2$—$CH_2$—$CH_2$— or $CF_3$—$CF_2$—$CF_2$—$CF_2$—$CF_2$—$CH_2$—$CH_2$—.

A straight-chain or branched perfluoroalkyl group having 1 to 8 C atoms is, for example, trifluoromethyl, pentafluoroethyl, heptafluoropropyl, heptafluoroisopropyl, n-nonafluorobutyl, sec-nonafluorobutyl, tert-nonafluorobutyl, dodecafluoropentyl, 1-, 2- or 3-trifluoromethyloctafluorobutyl, 1,1-, 1,2- or 2,2-bis(trifluoromethyl)pentafluoropropyl, 1-pentafluoroethylhexafluoropropyl, n-tridecafluorohexyl, n-pentadecafluoroheptyl or n-heptadecafluorooctyl. Preferred examples of the perfluorinated alkyl group $R_f$ are pentafluoroethyl, heptafluoropropyl, heptafluoroisopropyl, nonafluorobutyl, sec-nonafluorobutyl or tert-nonafluorobutyl.

Alk denotes a straight-chain or branched alkyl group having 1 to 12 C atoms, for example methyl, ethyl, isopropyl, propyl, butyl, sec-butyl or tert-butyl, furthermore pentyl, 1-, 2- or 3-methylbutyl, 1,1-, 1,2- or 2,2-dimethyl-propyl, 1-ethylpropyl, n-hexyl, n-heptyl, n-octyl, n-nonyl, n-decyl, n-undecyl or n-dodecyl. A straight-chain or branched alkyl group having 1 to 20 C atoms therefore consists of the said alkyl groups having 1 to 12 C atoms plus n-tridecyl, n-tetracecyl, n-pentadecyl, n-hexadecyl, n-heptadecyl, n-octadecyl, n-nonadecyl or n-eicosyl.

A straight-chain or branched alkenyl having 2 to 20 C atoms, where, in addition, a plurality of double bonds may be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl, hexenyl or decen-9-yl.

Ar denotes an aryl group having 6 to 12 C atoms, for example phenyl, naphthyl or anthracenyl, which may be unsubstituted or substituted by Hal, $NH_2$, $NAlk_2$, NHAlk, $NO_2$, CN, $SO_3H$ or OR. The substitution may take place once or a number of times by the substituents indicated, preferably once. The phenyl group is preferably substituted in the 4-position. Ar preferably corresponds to phenyl.

Ac denotes a carboxyl group OC(O)R, where R is as defined below or in other words the radical of a carboxylic acid. The carboxylic acid is in accordance with the invention not restricted with respect to the number of carboxyl groups, i.e. it also preferably includes aliphatic dicarboxylic acids, preferably having 1 to 6 C atoms, for example oxalic acid, malonic acid, succinic acid, glutaric acid or adipic acid. Since the dicarboxylic acids contain two reactive carboxyl groups which are available for a reaction, the compounds of the formula I likewise include the compounds of the formula Ib, as described above.

R' in the formula Ib denotes a single bond or an alkylene group having 1 to 4 C atoms, i.e. —$CH_2$—, —$(CH_2)_2$—, —$(CH_2)_3$— or —$(CH_2)_4$—. R' very particularly preferably stands for a single bond, i.e. complexes of oxalic acid form.

Het denotes a heteroaryl group having 5 to 13 C atoms, which may be unsubstituted or substituted by Hal, $NH_2$, $NAlk_2$, NHAlk, $NO_2$, CN, $SO_3H$ or OR, where the heteroatom is at least one O, S or N atom. It is also possible for a plurality of heteroatoms to be present. The substitution may take place once or a number of times by the substituents indicated, preferably once.

A straight-chain or branched alkenyl having 2 to 20 C atoms, where, in addition, a plurality of double bonds may be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl, hexenyl or decenyl.

Hal denotes F, Cl, Br or I, preferably F, Cl or Br, very particularly preferably F.

The number n denotes 1, 2 or 3, preferably 2 or 3, very particularly preferably 3.

R denotes H or a straight-chain or branched alkyl group having 1 to 20 C atoms, which may be partially substituted by Hal, $NH_2$, NHAlk, $NAlk_2$, $NO_2$, CN or $SO_3H$, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—.

The straight-chain or branched alkyl group in the definition of the substituent R preferably stands for a straight-chain or branched alkyl group having 1 to 8 C atoms, which may be partially substituted by Hal, $NH_2$ or OH and/or where one or two non-adjacent carbon atoms of the alkyl group which are not bonded to the heteroatom may be replaced by atoms and/or atom groups selected from the group —O—, —NH— or —C(O)—O—.

The straight-chain or branched alkenyl group in the definition of the substituent R preferably stands for a straight-chain or branched alkenyl group having 2 to 10 C atoms. The double bond is preferably terminal, for example in the case of dec-9-enyl.

R preferably denotes a straight-chain or branched alkyl group having 1 to 20 C atoms, which may be partially substituted by Hal, $NH_2$, NHAlk, $NAlk_2$, $NO_2$, CN or $SO_3H$, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—.

R particularly preferably stands for H, ethyl, 2,2,2-trifluoroethyl, hydroxy-ethyl, dec-9-enyl, —$CH_2$—$CH_2$—NH—$(CH_2)_3$—$NH_2$, —$(CH_2)_5$—C(O)—O—$CH_2$—$CH_3$, aminoethyl or methoxyethyl.

In the definition of Ac, R preferably stands for a straight-chain or branched alkyl group having 1 to 20 C atoms, particularly preferably for a straight-chain or branched alkyl group having 1 to 8 C atoms.

$R_f$ preferably stands, in each case independently of one another, for a straight-chain or branched perfluoroalkyl group having 1 to 8 C atoms, particularly preferably for a straight-chain or branched perfluoroalkyl group having 1 to 4 C atoms, very particularly preferably for a straight-chain or branched perfluoroalkyl group having 2 to 4 C atoms, in particular very particularly preferably for pentafluoroethyl or n-nonafluorobutyl.

All substituents $R_f$ are preferably identical.

X preferably stands for OR, Ac or OAr, particularly preferably for OR or Ac, very particularly preferably for OR.

Ac in formula I particularly preferably denotes O—C(O)$CH_3$. (OC(O)—R'—C(O)O) in formula Ib preferably denotes OC(O)—C(O)O.

OAr in formula I particularly preferably denotes O-phenyl or para-hydroxyphenyl.

If, in the case of the compounds of the formula I, a definition for the substituent X in which terminal OH groups are present is selected, it may be possible for this OH group to react again with the starting material and accordingly for compounds of the formula Ic to arise

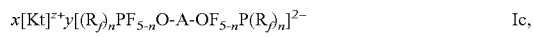

where x, y, z, Kt, $R_f$ and n have a meaning indicated in the case of the formula Ib and A denotes an arylene, heteroarylene, alkylene or alkenylene, corresponding to the descriptions of Ar, Het and R, for example preferably phenylene or ethylene.

Dimeric compounds of the formula Ic of this type are also covered by the formula I. The preparation of the compounds of the formula Ic can be controlled via the synthesis process, as described below.

The cation of the compounds of the formula I, as described above, is a stabilised proton, a metal cation, preferably an alkali-metal cation, an alkaline-earth metal cation or a cation from groups 3 to 12 of the Periodic Table, or an organic cation.

A stabilised proton is in accordance with the invention a proton which is stabilised by an organic base or a basic solvent. In the case of stabilisation by a basic solvent, the term solvated proton can also be used for the term stabilised proton.

Suitable organic bases for stabilisation of the proton in the compounds of the formula I are preferably selected from the group aromatic amine, dialkylformamide or dialkylacetamide, where the alkyl groups of the dialkylformamide or dialkylacetamide each have, independently of one another, 1 to 8 C atoms. The alkyl groups in the dialkylformamide or dialkylacetamide are preferably identical.

Preferred aromatic amines are, for example, pyridine, morpholine, piperazine, imidazole, oxazole or thiazole, each of which may be substituted by alkyl groups having 1 to 8 C atoms or dialkylamino groups, which each have, independently of one another, 1 to 8 C atoms. The aromatic amine is particularly preferably selected from the group pyridine, 4-methylpyridine or 4-dimethylaminopyridine.

Preferred dialkylformamides are, for example, dimethylformamide, diethylformamide, dipropylformamide. A particularly preferred dialkylformamide is dimethylformamide.

Preferred dialkylacetamides are, for example, dimethylacetamide, diethylacetamide or dipropylacetamide.

The proton is particularly preferably stabilised by an aromatic amine or dialkylformamide, as described above.

The proton is very particularly preferably stabilised by 4-dimethylaminopyridine or dimethylformamide. The proton is in particular very particularly preferably stabilised by 4-dimethylaminopyridine.

Suitable basic solvents for stabilisation of the proton in the compounds of the formula I are preferably selected from water, dialkyl ethers containing alkyl groups, which each have, independently of one another, 1 to 4 C atoms, aliphatic alcohols having 1 to 8 C atoms, ethyl acetate, acetonitrile, dimethyl sulfoxide or N-alkyl-2-pyrrolidone, where the alkyl group has 1 to 8 C atoms.

Preferred N-alkyl-2-pyrrolidones are, for example, N-methyl-2-pyrrolidone, N-ethyl-2-pyrrolidone, N-propyl-2-pyrrolidone or N-butyl-2-pyrrolidone.

There are no restrictions per se regarding the choice of the organic cation of the compound of the formula I or Ib or Ic in accordance with the resent invention. The organic cations are preferably selected from the group comprising ammonium, sulfonium, oxonium, phosphonium, uronium, thiouronium, guanidinium cations or are heterocyclic cations. Examples of organic cations are also polyammonium ions having a degree of charging z=4. Selected organic cations are represented by the formulae (1) to (8).

Ammonium cations can be described, for example, by the formula (1), sulfonium cations can be described, for example, by formula (2) or oxonium cations can be described, for example, by the formula (3), $$[N(R^0)_4]^+ \quad (1)$$

$$[S(R^0)_3]^+ \quad (2)$$

or $$[O(R^0)_3] \quad (3),$$

where $R^0$ in each case, independently of one another, denotes
H, where all substituents $R^0$ in the formula (2) cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms,
aryl having 6 to 12 C atoms, which may be substituted by straight-chain or branched alkyl groups having 1-6 C atoms, where $R_0$ may be partially substituted by halogen or partially substituted by $—OR^1$, $—C(O)OR^1$, $—OC(O)R^1$, $—OC(O)OR^1$, $—C(O)NR^1{}_2$ or $—SO_2NR^1{}_2$, and where one or two non-adjacent carbon atoms of the radical $R_0$ which are not in the α-position may be replaced by atoms and/or atom groups selected from the group $—O—$, $—S—$, $—S(O)—$, $—SO_2—$, $—N^+(R^1)_2—$, $—C(O)NR^1—$, $—SO_2NR^1—$ or $—P(O)R^1—$, in which $R^1$ stands for H, non- or partially fluorinated straight-chain or branched $C_1$- to $C_6$-alkyl, $C_3$- to $C_7$-cycloalkyl, unsubstituted or substituted phenyl.

Phosphonium cations can be described, for example, by the formula (4), $$[P(R^2)_4]^+ \quad (4),$$

where $R^2$ in each case, independently of one another, denotes
$N(R^{1*})_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms,
aryl having 6 to 12 C atoms, which may be substituted by straight-chain or branched alkyl groups having 1-6 C atoms, where $R^2$ may be partially substituted by halogen, or partially substituted by $—OR^1$, $—C(O)OR^1$, $—OC(O)R^1$, $—OC(O)OR^1$, $—C(O)NR^1{}_2$ or $—SO_2NR^1{}_2$, and where one or two non-adjacent carbon atoms of the $R^2$ which are not in the α-position may be replaced by atoms and/or atom groups selected from the group $—O—$, $—S—$, $—S(O)—$ or $—SO_2—$, in which $R^1$ stands for H, non- or partially fluorinated straight-chain or branched $C_1$- to $C_6$-alkyl, $C_3$- to $C_7$-cycloalkyl, unsubstituted or substituted phenyl and $R^{1*}$ stands for non- or partially fluorinated straight-chain or branched $C_1$- to $C_6$-alkyl, $C_3$- to $C_7$-cycloalkyl, unsubstituted or substituted phenyl.

Uronium cations can be described, for example, by the formula (5) or thiouronium cations can be described, for example, by the formula (6), $$[C(NR^3R^4)(OR^5)(NR^6R^7)]^+ \quad (5)$$

or $$[C(NR^3R^4)(SR^5)(NR^6R^7)]^+ \quad (6),$$

where
R³ to R⁷ each, independently of one another, denote
H or N(R¹*)₂,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms,
aryl having 6 to 12 C atoms, which may be substituted by straight-chain or branched alkyl groups having 1-6 C atoms,
where one or more of the substituents R³ to R⁷ may be partially substituted by halogen, or partially substituted by —OH, —OR¹, —CN, —C(O)NR¹₂, —SO₂NR¹₂, and where one or two non-adjacent carbon atoms of R³ to R⁷ which are not in the α-position may be replaced by atoms and/or atom groups selected from the group —O—, —S—, —S(O)—, —SO₂—, —N⁺(R¹)₂—, —C(O)NR¹—, —SO₂NR¹—, or —P(O)R¹—, in which R¹ stands for H, non- or partially fluorinated straight-chain or branched C₁- to C₆-alkyl, C₃- to C₇-cycloalkyl, unsubstituted or substituted phenyl and R¹* stands for non- or partially fluorinated straight-chain or branched C₁- to C₆-alkyl, C₃- to C₇-cycloalkyl, unsubstituted or substituted phenyl.

Guanidinium cations can be described, for example, by the formula (7),

[C(NR⁸R⁹)(NR¹⁰R¹¹)(NR¹²R¹³)]⁺    (7), where
R⁸ to R¹³ each, independently of one another, denote
H or N(R¹*)₂,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms,
aryl having 6 to 12 C atoms, which may be substituted by straight-chain or branched alkyl groups having 1-6 C atoms,
where one or more of the substituents R⁸ to R¹³ may be partially substituted by halogen, or partially substituted by —OR¹, —CN, —C(O)NR¹₂, —SO₂NR¹₂, and where one or two non-adjacent carbon atoms of R⁸ to R¹³ which are not in the α-position may be replaced by atoms and/or atom groups selected from the group —O—, —S—, —S(O)—, —SO₂—, —N⁺(R¹)₂—, —C(O)NR¹—, —SO₂NR¹—, or —P(O)R¹—, in which R¹ stands for H, non- or partially fluorinated straight-chain or branched C₁- to C₆-alkyl, C₃- to C₇-cycloalkyl, unsubstituted or substituted phenyl and R¹* stands for non- or partially fluorinated straight-chain or branched C₁- to C₆-alkyl, C₃- to C₇-cycloalkyl, unsubstituted or substituted phenyl.

Heterocyclic cations can be described, for example, by the formula (8)

[HetN]⁺    (8), where [HetN]⁺ is a heterocyclic cation selected from the group comprising

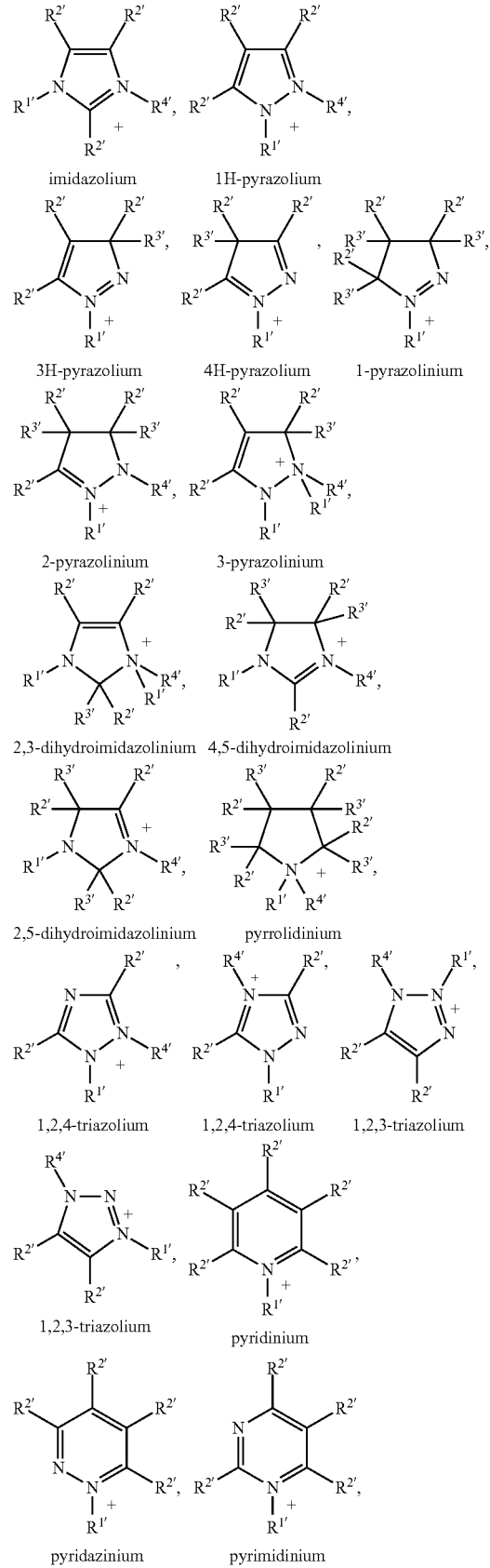

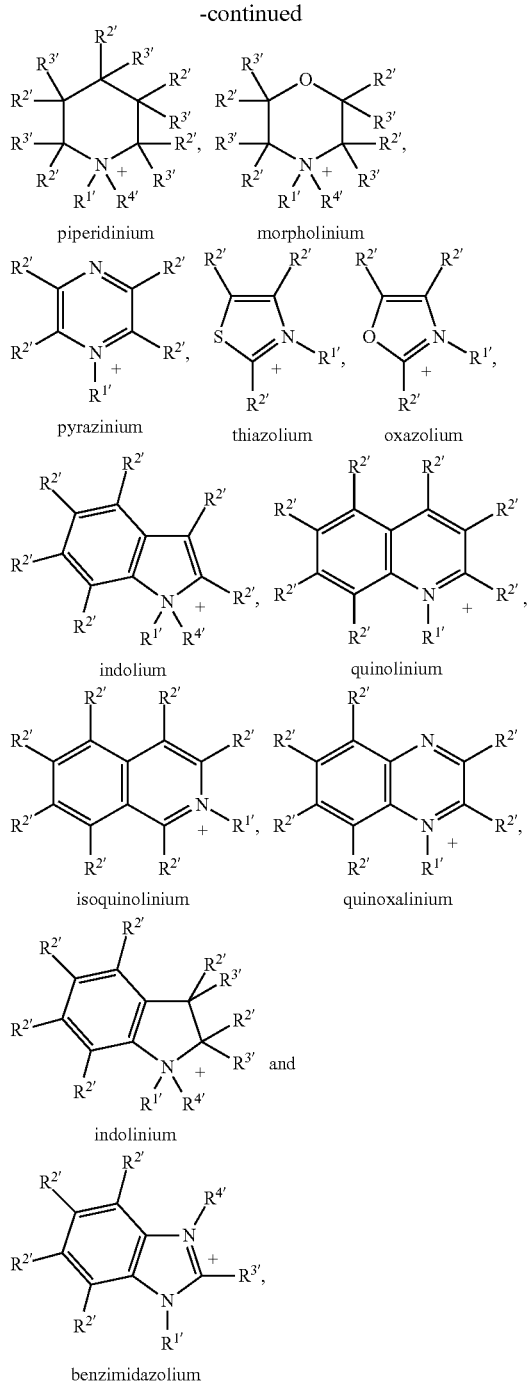

where the substituents R[1'] to R[4'] each, independently of one another, denote

H, straight-chain or branched alkyl having 1-20 C atoms, which may also be fluorinated or perfluorinated, straight-chain or branched alkenyl having 2-20 C atoms and one or more double bonds, which may also be fluorinated or perfluorinated, straight-chain or branched alkynyl having 2-20 C atoms and one or more triple bonds, which may also be fluorinated, saturated or partially unsaturated cycloalkyl having 3-7 C atoms, which may be substituted by straight-chain or branched alkyl groups having 1-6 C atoms, aryl having 6 to 12 C atoms, which may be substituted by straight-chain or branched alkyl groups having 1-6 C atoms, saturated, partially or fully unsaturated heteroaryl, heteroaryl-$C_1$-$C_6$-alkyl or aryl-$C_1$-$C_6$-alkyl, where the substituents R[1'], R[2'], R[3'] and/or R[4'] together may form a ring system, where one, two or three substituents R[1'] to R[4'] may be partially or fully substituted by halogens or partially by —$OR^1$, —CN, —C(O)$NR^1_2$, —$SO_2NR^1_2$, where the substituents R[1'] and R[4'] cannot be substituted simultaneously and fully by halogens, and where one or two non-adjacent carbon atoms of the substituents R[1'] to R[4'] which are not bonded to the heteroatom may be replaced by atoms and/or atom groups selected from the group —O—, —S—, —S(O)—, —$SO_2$—, —$N^+(R^1)_2$—, —C(O)$NR^1$—, —$SO_2NR^1$—, or —P(O)$R^1$—, in which $R^1$ stands for H, non- or partially fluorinated straight-chain or branched $C_1$- to $C_6$-alkyl, $C_3$- to $C_7$-cycloalkyl, unsubstituted or substituted phenyl and $R^{1*}$ stands for non- or partially fluorinated straight-chain or branched $C_1$- to $C_6$-alkyl, $C_3$- to $C_7$-cycloalkyl, unsubstituted or substituted phenyl.

Suitable substituents $R_0$ and $R^2$ to $R^{13}$ of the compounds of the formulae (1) to (7) are preferably in accordance with the invention: H, straight-chain or branched $C_1$- to $C_{20}$-, in particular straight-chain or branched $C_1$- to $C_{14}$-alkyl groups, saturated $C_3$- to $C_7$-cycloalkyl groups, which may be substituted by straight-chain or branched $C_1$- to $C_6$-alkyl groups, or phenyl, which may be substituted by straight-chain or branched $C_1$- to $C_6$-alkyl groups.

The substituents $R^0$ and $R^2$ in the compounds of the formula (2), (3) or (4) may be identical or different. In the case of compounds of the formulae (2), all substituents $R^0$ are preferably identical or two are identical and one substituent is different. In the case of compounds of the formula (3), all substituents $R^0$ are preferably identical. In the case of compounds of the formula (4), three or four substituents $R^2$ are preferably identical.

The substituents $R^0$ and $R^2$ are particularly preferably methyl, ethyl, isopropyl, propyl, butyl, sec-butyl, pentyl, hexyl, octyl, decyl or tetradecyl.

Up to four substituents of the guanidinium cation [C($NR^8R^9$)($NR^{10}R^{11}$)($NR^{12}R^{13}$)]$^+$ may also be connected in pairs in such a way that mono-, bi- or polycyclic molecules arise.

Without restricting generality, examples of such guanidinium cations are:

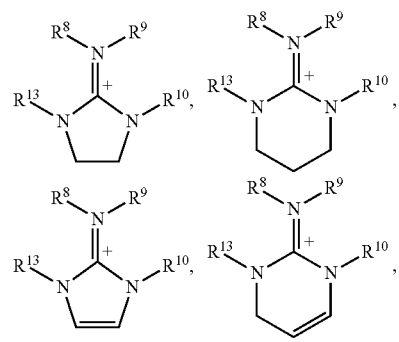

-continued

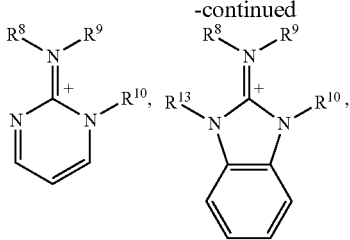

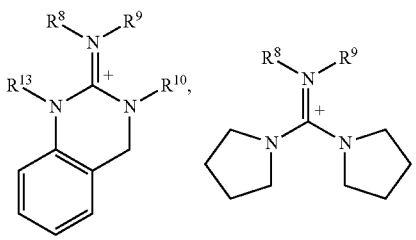

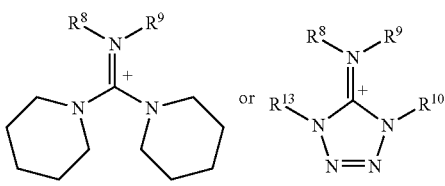

where the substituents $R^8$ to $R^{10}$ and $R^{13}$ can have a meaning or particularly preferred meaning indicated above.

If desired, the carbocycles or heterocycles of the guanidinium cations indicated above may also be substituted by straight-chain or branched $C_1$- to $C_6$-alkyl, $C_1$- to $C_6$-alkenyl, CN, $NR^1_2$, F, Cl, Br, I, straight-chain or branched $C_1$-$C_6$-alkoxy, $SCF_3$, $SO_2CF_3$ or $SO_2NR^1_2$, where $R^1$ has a meaning indicated above, substituted or unsubstituted phenyl or an unsubstituted or substituted heterocycle.

Up to four substituents of the thiouronium cation $[C(NR^3R^4)(SR^5)(NR^6R^7)]^+$ may also be bonded in pairs in such a way that mono-, bi- or polycyclic molecules are formed.

Without restricting generality, examples of such thiouronium cations are indicated below:

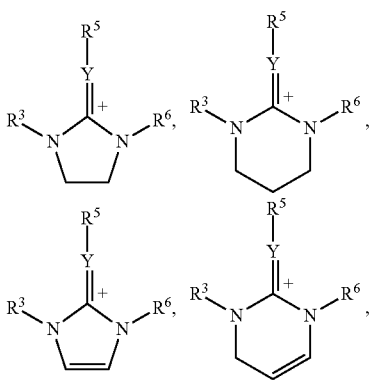

-continued

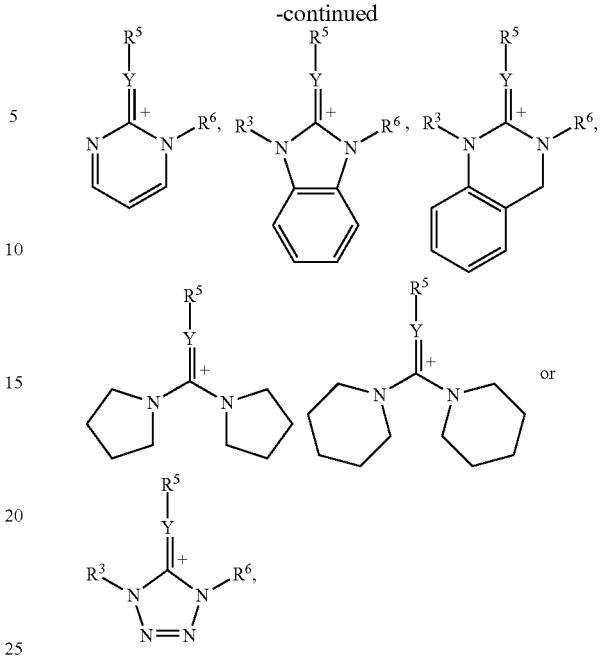

in which Y=S
and where the substituents $R^3$, $R^5$ and $R^6$ can have a meaning or particularly preferred meaning indicated above.

If desired, the carbocycles or heterocycles of the molecules indicated above may also be substituted by straight-chain or branched $C_1$- to $C_6$-alkyl, $C_1$- to $C_6$-alkenyl, CN, $NR^1_2$, F, Cl, Br, I, straight-chain or branched $C_1$-$C_6$-alkoxy, $SCF_3$, $SO_2CF_3$ or $SO_2NR^1_2$ or substituted or unsubstituted phenyl or an unsubstituted or substituted heterocycle, where $R^1$ has a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (5) to (7) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ and $R^{4'}$ of compounds of the formula (8) are preferably: straight-chain or branched $C_1$- to $C_{20}$, in particular straight-chain or branched $C_1$- to $C_{12}$-alkyl groups, saturated $C_3$- to $C_7$-cycloalkyl groups, which may be substituted by straight-chain or branched $C_1$- to $C_6$-alkyl groups, or phenyl, which may be substituted by straight-chain or branched $C_1$- to $C_6$-alkyl groups.

In accordance with the invention, suitable substituents $R^{2'}$ and $R^{3'}$ of compounds of the formula (8), besides H, are preferably: straight-chain or branched $C_1$- to $C_{20}$, in particular straight-chain or branched $C_1$- to $C_{12}$-alkyl groups.

The substituents $R^{1'}$ and $R^{4'}$ are each, independently of one another, particularly preferably methyl, ethyl, isopropyl, propyl, butyl, sec-butyl, pentyl, hexyl, octyl, decyl, cyclohexyl, phenyl or benzyl. They are very particularly preferably methyl, ethyl, n-butyl or hexyl. In pyrrolidine, piperidine, indoline, pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl. If the compounds are partially fluorinated, at least one H atom is replaced by an F atom. If the compounds are perfluorinated, all H atoms of the corresponding alkyl group are replaced by F atoms.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —$OR^1$, —$NR^1_2$, —CN, —$C(O)NR^1_2$, —$SO_2NR^1_2$ Unsubstituted saturated or partially unsaturated cycloalkyl groups having 3-7 C atoms are therefore cyclopropyl, cyclobutyl, cyclopentyl, cyclohexyl, cycloheptyl, cyclopentenyl, cyclohexenyl or cycloheptenyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —$OR^1$, —CN, —$C(O)NR^1_2$, —$SO_2NR^1_2$.

In the substituents $R^0$, $R^3$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —$SO_2$—, —$N^+(R^1)_2$—, —$C(O)NR^1$—, —$SO_2NR^1$—, or —$P(O)R^1$—, where $R^1$=H, non- or partially fluorinated straight-chain or branched $C_1$- to $C_6$-alkyl, $C_2$- to $C_7$-cycloalkyl, unsubstituted or substituted phenyl.

Without restricting generality, examples of substituents $R^0$, $R^2$ to $R^{13}$ and $R^{1'}$ to $R^{4'}$ modified in this way are:
—$OCH_3$, —$OCH(CH_3)_2$, —$CH_2OCH_3$, —$CH_2$—$CH_2$—O—$CH_3$, —$C_2H_4OCH(CH_3)_2$, —$C_2H_4SC_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_2SO_2CF_3$, —$C_2F_4N(C_2F_5)$ $C_2F_5$, —$CHF_2$, —$CH_2CF_3$, —$C_2F_2H_3$, —$C_3H_6$, —$CH_2C_3F_7$, —$C(CFH_2)_3$, —$CH_2C_6H_5$ or $P(O)(C_2H_5)_2$.

In $R^1$, $C_3$- to $C_7$-cycloalkyl is, for example, cyclopropyl, cyclobutyl, cyclopentyl, cyclohexyl or cycloheptyl.

In $R^1$, substituted phenyl denotes phenyl which is substituted by $C_1$- to $C_6$-alkyl, $C_1$- to $C_6$-alkenyl, F, Cl, Br, I, —$C_1$-$C_6$-alkoxy, $NR''_2$, —$SR''$, —$S(O)R''$, —$SO_2R''$ or $SO_2NR''_2$, where R* denotes F, Cl or Br and R" denotes a non-, partially or perfluorinated $C_1$- to $C_6$-alkyl or $C_3$- to $C_7$-cycloalkyl as defined for $R^1$, for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-methoxyphenyl, o-, m- or p-ethoxyphenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, CN, $NR^1_2$, F, Cl, Br, I, $C_1$-$C_6$-alkoxy, $SCF_3$, $SO_2CF_3$ or $SO_2NR^1_2$, where $R^1$ has a meaning indicated above.

The heterocyclic radical or Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocycles described above may furthermore be linked to the alkylene chain in this way.

$HetN^+$ is preferably

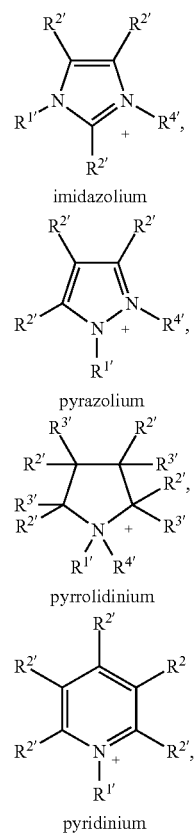

imidazolium pyrazolium pyrrolidinium pyridinium

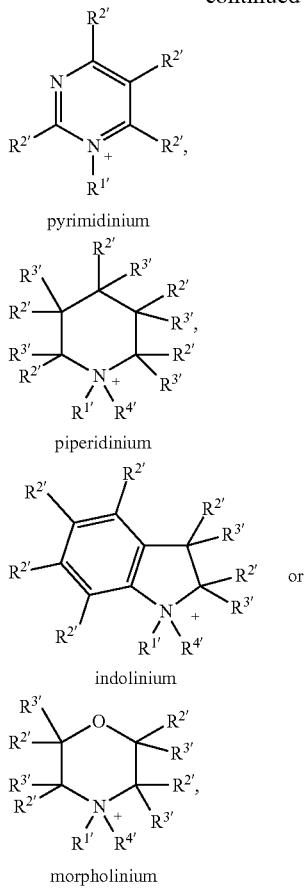

pyrimidinium piperidinium indolinium morpholinium where the substituents $R^{1'}$ to $R^{4'}$ each, independently of one another, have a meaning described above.

The organic cation $[Kt]^{x+}$ is particularly preferably selected from the group comprising imidazolium, pyridinium, pyrrolidinium, ammonium or phosphonium cations, as defined above.

Particularly suitable cations are selected from the group tetraalkylammonium, 1,1-dialkylpyrrolidinium, 1-alkyl-1-alkoxyalkylpyrrolidnium or 1,3-dialkylimidazolium, where the alkyl groups or the alkoxy group in the alkoxyalkyl group may each, independently of one another, have 1 to 10 C atoms. The alkly groups very particularly preferably have 1 to 6 C atoms and the alkoxy group very particularly preferably has 1 to 3 C atoms. The alkyl groups in tetraalkylammonium may therefore be identical or different. Preferably, three alkyl groups are identical and one alkyl group is different or two alkyl groups are identical and the other two are different. Preferred tetraalkylammonium cations are, for example, trimethyl(ethyl)-ammonium, triethyl(methyl)ammonium, tripropyl(methyl)ammonium, tributyl-(methyl)ammonium, tripentyl(methyl)ammonium, trihexyl(methyl)ammonium, triheptyl(methyl)ammonium, trioctyl(methyl)ammonium, trinonyl-(methyl)ammonium, tridecyl(methyl)ammonium, trihexyl(ethyl)ammonium, ethyl(trioctyl)ammonium, propyl (dimethyl)ethylammonium, butyl(dimethyl)-ethylammonium, methoxyethyl(dimethyl)ethylammonium, methoxyethyl-(diethyl)methylammonium, methoxyethyl(dimethyl) propylammonium, ethoxyethyl(dimethyl)ethylammonium. Particularly preferred quaternary ammonium cations are propyl(dimethyl)ethylammonium and/or methoxyethyl(dimethyl)ethylammonium.

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1-1-dinonylpyrrolidinium, 1-nony-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-methoxyethyl-1-methylpyrrolidinium, 1-methoxyethyl-1-ethylpyrrolidinium, 1-methoxyethyl-1-propylpyrrolidinium, 1-methoxyethyl-1-butylpyrrolidinium, 1-ethoxyethyl-1-methylpyrrolidinium, 1-ethoxymethyl-1-methylpyrrolidinium. Very particular preference is given to 1-methoxyethyl-1-methylpyrrolidinium.

Preferred 1,3-dialkylimidazolium cations are, for example, 1-ethyl-3-methylimidazolium, 1-methyl-3-propylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropypylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Particularly preferred 1-alkenyl-3-alkylimidazolium cations are 1-allyl-3-methylimidazolium or 1-allyl-2,3-dimethylimidazolium.

The organic cations of the compounds of the formula I are preferably heterocyclic cations of the formula (8), where HetN$^{z+}$ is imidazolium, pyrrolidinium or pyridinium, with substituents $R^{1'}$ to $R^{4'}$, each of which has, independently of one another, a meaning indicated or indicated as preferred. The organic cation of the compounds of the formula I are particularly preferably imidazolium, where the substituents $R^{1'}$ to $R^{4'}$ have a meaning mentioned above or a meaning indicated as preferred or they have the meaning of the meanings preferably indicated for 1,1-dialkylpyrrolidinium, 1-alkyl-1-alkoxyalkylalkylpyrrolidinium, 1,3-dialkylimidazolium, 1-alkenyl-3-alkylimidazolium or 1-alkoxyalkyl-3-alkylimidazolium, as described above.

Particularly preferred organic cations of the formula I are accordingly 1-butyl-1-methylpyrrolidinium, 1-ethyl-3-methylimidazolium, 1-ethyl-2,3-dimethylimidazolium, 1-butyl-2,3-dimethylimidazolium, 1-(2-methoxyethyl)-3-methylimidazolium, 1-butyl-3-methylimidazolium, tributylmethylammonium, tetra-n-butylammonium, tributylmethylphosphonium, tetraphenylphosphonium, tetrabutylphosphonium, diethylmethylsulfonium, S-ethyl-N,N,N', N'-tetramethylisothiouronium, 1-allyl-3-methylimidazolium, 1-allyl-2,3-dimethylimidazolium, 1-cyanomethyl-3-methylimidazolium, 1-(2-cyanoethyl)-3-methylimidazolium, 1-methyl-3-propynylimidazlium, 1-butyl-4-methylpyridinum, 1,1-dimethylpyrrolidinium or trimethylsulfonium.

An alkali-metal cation is a lithium cation, a sodium cation, a potassium cation, a rubidium cation or a caesium cation, in particular a lithium cation, a sodium cation or a potassium cation.

An alkaline-earth metal cation is a magnesium cation, a calcium cation, a strontium cation or a barium cation, preferably a magnesium cation or a calcium cation.

A metal cation from group 3 to 12 of the Periodic Table is, for example, a cation of the metals silver, copper, yttrium, ytterbium, lanthanum, scandium, cerium, neodymium, terbium, samarium, rhodium, rhutenium, iridium, palladium, platinum, osmium, cobalt, nickel, iron, chromium, molybdenum, tungsten, vanadium, titanium, zirconium, hafnium, thorium, uranium or gold, where the corresponding metal cations in solvated form or stabilised by ligands are also included.

Particularly preferred metal cations are Li, Na$^+$, K$^+$, Mg$^{2+}$, Ca$^{2+}$, Ag$^+$, Cu$^+$, Y$^{+3}$, Yb$^{+3}$, La$^{+3}$, Sc$^{+3}$, Ce$^{+2}$, Pt$^{+2}$ or Pd$^{+2}$ A suitable starting material for the synthesis of the compounds of the formula I are fluoroalkylfluorophosphoranes.

The invention accordingly furthermore relates to a process for the preparation of compounds of the formula I, as described above, where Kt denotes a proton which is stabilised by an organic base, characterised in that a fluoroalkylfluorophosphorane of the formula II $(R_f)_n PF_{5-n}$     II, where $R_f$ in each case, independently of one another, denotes a straight-chain or branched fluoroalkyl group having 1 to 8 C atoms and n denotes 1, 2 or 3, is reacted with an organic base, where a compound of the formula IIIa, IIIb or IIIc arises

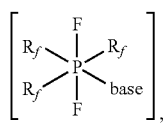
IIIa

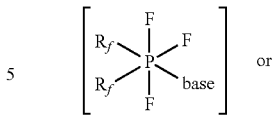
IIIb

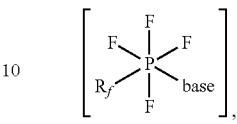
IIIc where $R_f$ in each case, independently of one another, has a meaning indicated above and the compound of the formula IIIa, IIIb or IIIc or a tautomeric or stereoisomeric form thereof is subsequently reacted with HX, where X denotes OR, Ac, OAr or OHet, Ac denotes a carboxyl group OC(O)R, Alk denotes a straight-chain or branched alkyl group having 1 to 12 C atoms, Ar denotes an aryl group having 6 to 12 C atoms, which may be unsubstituted or substituted by Hal, NH$_2$, NAlk$_2$, NHAlk, NO$_2$, CN, SO$_3$H or OR, Het denotes a heteroaryl group having 5 to 13 C atoms, which may be unsubstituted or substituted by Hal, NH$_2$, NAlk$_2$, NHAlk, NO$_2$, CN, SO$_3$H or OR, R denotes H or a straight-chain or branched alkyl group having 1 to 20 C atoms, which may be partially substituted by Hal, NH$_2$, NHAlk, NAlk$_2$, NO$_2$, CN or SO$_3$H, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —SO$_2$—, NH, —C(O)—, —O—C(O)— or —C(O)—O—.

HX in this process may also be an aliphatic dicarboxylic acid, where this reaction results in compounds of the formula Ib, as described above in the case of the compounds of the formula I.

The preparation of perfluoroalkylfluorophosphoranes of the formula II can be carried out by conventional methods known to the person skilled in the art. These compounds are preferably prepared by electrochemical fluorination of suitable starting compounds [V. Y. Semenii et al., 1985, Zh. Obshch. Khim. 55 (12): 2716-2720; N. V. Ignatyev, P. Sartori, 2000, J. Fluorine Chem. 103: 57-61; WO 00/21969].

Fluoroalkylfluorophosphoranes can be obtained by free-radical addition of dialkyl phosphites, (RO)$_2$P(O)H or phosphines onto fluoroolefins [N. O. Brace, J. Org. Chem., 26 (1961), p. 3197-3201; P. Cooper, R. Fields, R. N. Haszeldine, J. Chem. Soc., Perkin 1, 1975, p. 702-707; G. M. Burch, H. Goldwhite, R. N. Haszeldine, J. Chem. Soc., 1963, p. 1083-1091] or to fluoroalkylolefins see P. Kirsch, Modern Fluoroorganic Chemistry, WILEY-VCH, 2004, p. 174], following a chlorination/fluorination or an oxidative fluorination.

The reaction of the phosphorane of the formula II with the organic base, in particular the organic bases, as described above or as preferably described, is carried out at temperatures of 0 to 80° C., preferably 15 to 30° C., in the presence of an organic solvent and in a water-free atmosphere.

Suitable solvents here are acetonitrile, dioxane, dichloromethane, dimethoxyethane, dimethyl sulfoxide, tetrahydrofuran or dialkyl ethers, for example diethyl ether or methyl t-butyl ether.

The compounds of the formulae IIIa, IIIb or IIIc can be isolated, but are preferably not isolated, but instead reacted further in a subsequent reaction, without work-up of the reaction mixture, with the compound HX, where X has a meaning indicated above or described as preferred.

The reaction temperature of the reaction with the compound HX is also 0 to 80° C., preferably 15 to 30° C., particularly preferably room temperature. If the compound HX carries more than one OH group, then, depending on the molar amount of the compound HX, only one OH group reacts with the phosphorane of the formula II, or a plurality of OH groups react with the phosphorane of the formula II. Examples in this respect are described in the example part.

Starting from the compounds of the formula I, where the cation is a proton which is stabilised by an organic base, it is then possible to prepare the compounds of the formula I with the cations selected from proton which is stabilised by basic solvents (solvated), metal cation or organic cations, as described above.

This is carried out classically for the metal cations or organic cations by a salt-exchange reaction.

The compounds of the formula I which have a proton which is stabilised by a basic solvent may also be formed in the process already described, depending on whether the affinity of the proton is preferably with the basic solvent or the organic base. The invention therefore furthermore relates to a process for the preparation of compounds of the formula I, as described above, where Kt denotes a metal cation or an organic cation, by a salt-exchange reaction, characterised in that a compound of the formula I, where Kt denotes a proton which is stabilised by a base, prepared by the process described above, is reacted with a compound of the formula IV $$KtA \qquad IV,$$

where Kt denotes a metal cation or an organic cation, as described above or as preferably described, and
A denotes an anion selected from $Cl^-$, $Br^-$, $I^-$, $OH^-$, $[R_1COO]^-$, $[R_1SO_3]^-$, $[R_2COO]^-$, $[R_2SO_3]^-$, $[R_1OSO_3]^-$, $[BF_4]^-$, $[SO_4]^{2-}$, $[HSO_4]^{1-}$, $[NO_3]^-$, $[(R_2)_2P(O)O]^-$, $[R_2P(O)O_2]^{2-}$ or $[CO_3]^{2-}$, where $R_1$ in each case, independently of one another, denotes straight-chain or branched alkyl having 1 to 4 C atoms and $R_2$ in each case, independently of one another, denotes straight-chain or branched perfluorinated alkyl having 1 to 4 C atoms, where the electroneutrality of the salts of the formula KtA must be observed.

The salt-exchange reaction is advantageously carried out in water, where temperatures of 0°-100° C., preferably 15-60° C., are suitable. The reaction is particularly preferably carried out at room temperature (25° C.).

However, the reaction may alternatively also be carried out in organic solvents at temperatures between −30° and 100° C. Suitable solvents here are acetonitrile, dioxane, dichloromethane, dimethoxyethane, dimethyl sulfoxide, tetrahydrofuran, dimethylformamide or alcohol, for example methanol, ethanol or isopropanol.

The salt-exchange reaction may also be carried out directly after the process described above without the need for isolation of the compounds of the formula I whose cation is a proton which is stabilised by an organic base.

The said salt-exchange reaction enables the preparation of compounds of the formula I, as described above, in which the metal cation is an alkali-metal or alkaline-earth metal cation. Of particular interest are compounds of the formula I, as described above, having alkali-metal or alkaline-earth metal cations in which X denotes OR or Ac, in particular compounds of the formula I having alkali-metal or alkaline-earth metal cations in which R in the radical OR does not denote H, but instead has the other meanings, as described above.

In particular, lithium salts of the compounds of the formula I, abbreviated to formula I-1

$$Li^+[P(R_f)_nF_{5-n}X]^- \qquad \text{I-1,}$$

where $R_f$ in each case, independently of one another, denotes a straight-chain or branched fluoroalkyl group having 1 to 8 C atoms,
X denotes OR, Ac, OAr or OHet,
Ac denotes a carboxyl group OC(O)R, also including salts of an aliphatic dicarboxylic acid having the formula Ib-1

$$2[Li]^+[(R_f)_nPF_{5-n}(OC(O)-R'-C(O)O)F_{5-n}P(R_f)_n]^{2-} \qquad \text{Ib-1}$$

and R' denotes a single bond or an alkylene group having 1 to 4 C atoms,
Alk denotes a straight-chain or branched alkyl group having 1 to 12 C atoms,
Ar denotes an aryl group having 6 to 12 C atoms, which may be unsubstituted or substituted by Hal, $NH_2$, $NAlk_2$, NHAlk, $NO_2$, CN, $SO_3H$ or OR,
Het denotes a heteroaryl group having 5 to 13 C atoms, which may be unsubstituted or substituted by Hal, $NH_2$, $NAlk_2$, NHAlk, $NO_2$, CN, $SO_3H$ or OR,
R denotes H, a straight-chain or branched alkyl group having 1 to 20 C atoms, which may be partially substituted by Hal, $NH_2$, NHAlk, $NAlk_2$, OH, $NO_2$, CN or $SO_3H$, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—,
Hal denotes F, Cl, Br or I and
n denotes 1, 2 or 3, and/or tautomers or stereoisomers thereof, including mixtures thereof in all ratios,
are suitable for the preparation of electrolyte preparations, in particular for electrochemical or opto-electronic devices. The lithium salts of the formula I-1 are suitable, in particular, as conductive salt for electrochemical batteries, in particular lithium-ion batteries, lithium-ion capacitors or lithium batteries. Particular preference is given to the use of lithium salts of the formula I-1 in which R denotes a straight-chain or branched alkyl group having 1 to 20 C atoms, which may be partially substituted by Hal, $NH_2$, NHAlk, $NAlk_2$, OH, $NO_2$, CN or $SO_3H$, or denote a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—.

Compounds of the formula I in which $Kt^{z+}$ denotes an alkali-metal or alkaline-earth metal cation and X denotes OR and R denotes H can be stored at low temperatures, but decompose on heating and/or in the presence of water without or in the presence of a base. These compounds are formed alternatively to the process described above if an inorganic base, preferably an alkali-metal hydroxide, an alkaline-earth metal hydroxide and/or an alkali-metal carbonate or alkaline-earth metal carbonate, is reacted with the phosphorane of the formula II, as described above. This is independent of the reaction temperature used.

Compounds of the formula I in which $Kt^{z+}$ denotes an alkali metal or an alkaline-earth metal cation and X denotes Ac are formed alternatively if an alkali-metal carboxylate or alkaline-earth metal carboxylate, as described above, is reacted with the phosphorane of the formula II, as described above, in the presence of an organic solvent.

Compounds of the formula I in which $Kt^{z+}$ corresponds to an ammonium cation of the formula (1), as described above, and X denotes Ac or compounds of the formula Ib in which $Kt^{z+}$ denotes an ammonium cation can alternatively be prepared by reacting a fluoroalkylfluorophosphorane of the formula II $$(R_f)_n PF_{5-n} \qquad \text{II,}$$

where $R_f$ in each case, independently of one another, denotes a straight-chain or branched fluoroalkyl group having 1 to 8 C atoms and n denotes 1, 2 or 3, with an ammonium carboxylate of the formula Va or Vb $$[N(R^0)_4]^+[(OC(O)R)]^- \qquad \text{Va or}$$

$$2[N(R^0)_4]^+[(OC(O)-R'-C(O)O)]^{2-} \qquad \text{Vb,}$$

where $R^0$, R and R' have an above-described or preferred meaning, in an organic solvent and subsequently removing the solvent.

Compounds of the formula I in which $Kt^{z+}$ corresponds to an ammonium cation of the formula (1) or a phosphonium cation of the formula (2), as described above, and X denotes OR and R denotes H can alternatively be prepared by reacting a fluoroalkylfluorophosphorane of the formula II $$(R_f)_n PF_{5-n} \qquad \text{II,}$$

where $R_f$ in each case, independently of one another, denotes a straight-chain or branched fluoroalkyl group having 1 to 8 C atoms and n denotes 1, 2 or 3, with an ammonium hydroxide of the formula VIa or a phosphonium hyroxide of the formula VIb $$[N(R^0)_4][OH] \qquad \text{VIa or}$$

$$[P(R^2)_4][OH] \qquad \text{VIb,}$$

where $R^0$ and $R^2$ have an above-mentioned or particularly preferred meaning, in an organic solvent and removing the organic solvent.

The compounds of the formula I, as described above, in which the cation Kt is a stabilised (solvated) proton, as described above, are particularly suitable as acid catalyst for chemical reactions, in particular for polymerisations and isomerisations.

The compounds of the formula I, as described above, in which Kt is a metal cation from groups 3 to 12 of the Periodic Table are particularly suitable as catalyst or as additive in electrolytes.

The compounds of the formula I, as described above, in which Kt is an organic cation, as described above or as preferably described, are particularly suitable as solvent or solvent additive, as catalyst or phase-transfer catalyst, as conductive salt or as electrolyte constituent, as fluorosurfactant, as heat-exchange medium, as separating agent or extractant, as antistatic, as plasticiser, as lubricant or constituent of lubricating oils or greases, as hydraulic fluid or additive for hydraulic fluids, as flameproofing agent or as additive in fire-extinguishing agents.

The compounds of the formula I having organic cations, as described above, are likewise ionic liquids.

In the case of the use of the compounds of the formula I as solvents, these are suitable in any type of reaction known to the person skilled in the art, for example for transition metal- or enzyme-catalysed reactions, such as, for example, hydroformylation reactions, oligomerisation reactions, esterifications or isomerisations, where the said list is not exhaustive.

In the case of the use as extractant, the compounds of the formula I can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials, as flame retardant for a number of materials or applications, and as conductive salt or additive in various electrochemical cells and applications, for example in galvanic cells, in capacitors or in fuel cells.

Further areas of applications of the compounds of the formula I in accordance with this invention are solvents for carbohydrate-containing solids, in particular biopolymers and derivatives or degradation products thereof. In addition, these novel compounds can be used as lubricants, working media for machines, such as compressors, pumps or hydraulic devices. A further area of application is the field of particle or nanomaterial synthesis, where these ionic liquids can act as medium or additive.

The compounds of the formula I with organic cations, for example ionic liquids in accordance with this invention, can preferably be used in electrochemical and/or opto-electronic devices, in particular in electrolyte formulations.

The present invention therefore furthermore relates to an electrolyte formulation comprising at least one compound of the formula I as described or preferably described above.

Electrolyte formulations of compounds of the formula I in which $[Kt]^{z+}$ denotes $Li^+$ or an organic cation can preferably be used in primary batteries, secondary batteries, capacitors, supercapacitors or electrochemical cells, optionally also in combination with further conductive salts and/or additives, as constituent of a polymer electrolyte or phase-transfer medium. Preferred batteries are lithium batteries or lithium ion batteries. A preferred capacitor is a lithium ion capacitor. The corresponding preferred lithium compounds have been described above and apply correspondingly.

Electrolyte formulations of compounds of the formula I can preferably be used in electrochemical and/or optoelectronic devices, such as a photovoltaic cell, a light-emitting device, an electrochromic or photoelectrochromic device, an electrochemical sensor and/or biosensor, particularly preferably in a dye-sensitised solar cell.

Such electrolyte formulations represent a crucial part of the devices disclosed and the performance of the device is substantially dependent on the physical and chemical properties of the various components of these electrolytes.

Electrolyte formulations according to the invention represent alternatives to already known electrolyte formulations. In particular in the field of electrolyte formulations of dye-sensitised solar cells, they have increased power-conversion efficiency, in particular at low temperature. The advantage of the use of perfluoroalkylcyanomethoxyfluoroborate is its low viscosity and accordingly the lower Nernst diffusion resistance of the oxidant species, in particular at lower temperature.

WO 2007/093961 and WO 2009/083901 describe the best power-conversion efficiencies to date in ionic liquid-based electrolytes comprising a significant amount of organic salts with tetracyanoborate (TCB) anions.

In chemical terms, an electrolyte is any substance which contains free ions and is consequently electrically conductive. The most typical electrolyte is an ionic solution, but molten and solid electrolytes are likewise possible. An electrolyte formulation according to the invention is therefore an electrically conductive medium, principally due to the presence of at least one substance which is in dissolved and/or molten state, i.e. supports an electrical conductivity through the movement of ionic species.

Typical molarities of the compounds of the formula I, as described above, in the electrolyte formulations are in the range from 0.1 to 3.5 M, preferably in the range from 0.8 to 2.5 M.

The molarity is preferably achieved with at least one compound of the formula I in which $[Kt]^{z+}$ denotes an organic cation as described or preferably described above.

For the purpose of the present invention, the molarity relates to the concentration at 25° C.

Other components of the electrolyte formulation are one or several further salts, solvents, iodine and others, as indicated below.

If the electrolyte formulation is a two-component system, it comprises two salts, one further salt and a compound of the formula I as described above. If the electrolyte formulation is a three-component system, it comprises two further salts and a compound of the formula I as described above. The two-component system comprises 90-20% by weight, preferably 80-55% by weight, particularly preferably 70-60% by weight of the further salt and 10-80% by weight, preferably 20-45% by weight or particularly preferably 30-40% by weight of the compound of the formula I as described above. The percentage data in this paragraph relate to the total amount (=100% by weight) of the salts present in the electrolyte formulation according to the invention. Amounts of further, generally optional components (additives) indicated below, such as, for example, N-containing compounds having free electron pairs, iodine, solvents, polymers, and nanoparticles, are not taken into account therein. The same percentage data apply to three-component or four-component systems, which means the total amount of the further salts must be used in the ranges indicated, for example two further ionic liquids are present, for example, in an amount of 90-20% by weight in the electrolyte formulation according to the invention.

According to a further embodiment of the present invention, the electrolyte formulation comprises at least one further salt with organic cations containing a quaternary nitrogen and an anion selected from a halide ion, such as F⁻, Cl⁻, I⁻, a polyhalide ion, a fluoroalkanesulfonate, a fluoroalkanecarboxylate, a tri(fluoroalkylsulfonyl)methide, a bis(fluoroalkylsulfonyl)imide, a nitrate, a hexafluorophosphate, a tris-, bis- or mono(fluoroalkyl)fluorophosphate, a tetrafluoroborate, a dicyanodifluoroborate, a tricyanofluoroborate, a tris-, bis- or mono(perfluoroalkyl)cyanoborate, a bis- or monocyanoperfluoroalkylmono- or bis fluoroborate, a perfluoroalkylalkoxyfluorocyanoborate or a perfluoroalkylalkoxydicyanoborate, a dicyanamide, a tricyanomethide, a tetracyanoborate, a thiocyanate, an alkylsulfonate or an alkylsulfate, where fluoroalkane has 1 to 20 C atoms, preferably perfluorinated, fluoroalkyl has 1 to 20 C atoms and alkyl has 1 to 20 C atoms. Fluoroalkane or fluoroalkyl is preferably perfluorinated.

The further salts are preferably selected from salts containing anions such as iodide, thiocyanate or tetracyanoborate, particularly preferred further salts are iodides.

The cation of the at least one further salt or of a preferred further salt can be selected from organic compounds containing a quaternary nitrogen atom, preferably cyclic organic cations, such as pyridinium, imidazolium, triazolium, pyrrolidinium or morpholinium.

However, in order to limit the amount of different cations in the electrolyte formulations, in particular for DSC, the organic cations can be selected from the definitions for the cations of the compounds of the formula I. According to a further preferred embodiment of the present invention, the electrolyte formulation therefore comprises at least one compound of the formula I as described above and at least one further iodide, in which the organic cations are selected, independently, from the group

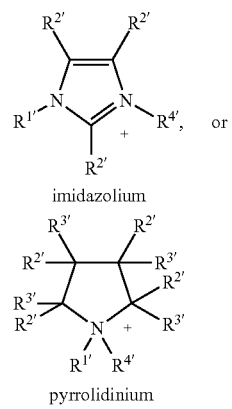

in which the substituents $R^{1'}$ to $R^{4'}$ have a meaning as described or preferably described above.

Particularly preferred examples of the at least one further salt are 1-ethyl-3-methylimidazolium iodide, 1-(2-methoxyethyl)-3-methylimidazolium iodide, 1-propyl-3-methylimidazolium iodide, 1-butyl-3-methyl-imidazolium iodide, 1-hexyl-3-methylimidazolium iodide, 1,3-dimethyl-imidazolium iodide, 1-allyl-3-methylimidazolium iodide, N-butyl-N-methyl-pyrrolidinium iodide or N,N-dimethyl-pyrrolidinium iodide.

In a further embodiment of the invention, guanidinium thiocyanate can be added to the electrolyte formulation according to the invention.

The electrolyte formulation of the invention preferably comprises iodine ($I_2$). Preferably, it comprises 0.01 to 50% by weight, more preferably 0.1 to 20% by weight and most preferably 1 to 10% by weight of $I_2$.

In a preferred embodiment, the electrolyte formulation of the present invention furthermore comprises at least one compound containing a nitrogen atom having free electron pairs. Examples of such compounds are found in EP 0 986 079 A2, starting on page 2, line 40-55, and further from page 3, lines 14 to page 7, line 54, which are incorporated herein by way of reference. Preferred examples of compounds having free electron pairs include imidazole and derivatives thereof, in particular benzimidazole and derivatives thereof.

The electrolyte formulation of the present invention comprises less than 50% of an organic solvent. The electrolyte formulation preferably comprises less than 40%, particularly preferably less than 30%, still more preferably less than 20% and even less than 10%. The electrolyte formulation most preferably comprises less than 5% of an organic solvent. For example, it is essentially free from an organic solvent. Percentage data relate to % by weight.

Organic solvents, if present in the amounts indicated above, can be selected from those disclosed in the literature. The solvent, if present, preferably has a boiling point above 160 degrees Celsius, particularly preferably above 190 degrees, such as propylene carbonate, ethylene carbonate, butylene carbonate, γ-butyrolactone, γ-valerolactone, glutaronitrile, adiponitrile, N-methyloxazolidinone, N-methylpyrrolidinone, N,N'-dimethylimidazolidinone, N,N-dimethylacetamide, cyclic ureas, preferably 1,3-dimethyl-2-imidazolidinone or 1,3-dimethyl-3,4,5,6-tetrahydro-2(1H)pyrimidinone, tetraglyme, sulfolanes, sulfones, which are preferably asymmetrically substituted, for example 2-ethanesulfonylpropane, 1-ethanesulfonyl-2-methylpropane or 2-(propane-2-sulfonyl)-butane, 3-methylsulfolane, dimethyl sulfoxide, trimethyl phosphate and methoxy-substituted nitriles. Other possible solvents are acetonitrile, benzonitrile or valeronitrile.

If a solvent is present in the electrolyte formulation, a polymer may furthermore be present as gelling agent, where the polymer is polyvinylidene fluoride, polyvinylidene-hexafluoropropylene, polyvinylidene-hexafluoropropylene-chlorotrifluoroethylene copolymers, nafion, polyethylene oxide, polymethyl methacrylate, polyacrylonitrile, polypropylene, polystyrene, polybutadiene, polyethylene glycol, polyvinylpyrrolidone, polyaniline, polypyrrole, polythiophene. These polymers are added to electrolyte formulations in order to convert liquid electrolytes into quasi-solid or solid electrolytes and thus to improve the solvent retention, especially during ageing.

The electrolyte formulation of the invention may furthermore comprise metal-oxide nanoparticles, such as, for example, $SiO_2$, $TiO_2$, $Al_2O_3$, MgO or ZnO, which can also increase the solidity and thus the solvent retention.

The electrolyte formulation of the invention has many applications. For example, it can be used in an opto-electronic and/or electrochemical device, such as a photoelement, a light-emitter device, an electrochromic or photo-electrochromic device, an electrochemical sensor and/or biosensor. Use in electrochemical batteries is also possible, for example in a lithium ion battery or a double-layer capacitor.

The present invention therefore relates furthermore to the use of the electrolyte formulation as described in detail above in an electrochemical and/or opto-electronic device which is a photoelement, a light-emitter device, an electrochromic or photo-electrochromic device, an electrochemical sensor and/or biosensor. The electrolyte formulation can preferably be used in dye-sensitised solar cells.

The present invention therefore relates furthermore to an electrochemical and/or opto-electronic device, for example a photoelement, a light-emitter device, an electrochromic or photo-electrochromic device, an electrochemical sensor and/or biosensor comprising an electrolyte formulation comprising at least one compound of the formula I $$Kt^{z+}{}_z[P(R_f)_n F_{5-n} X]^-  \qquad \text{I,}$$

where $R_f$ in each case, independently of one another, denotes a straight-chain or branched fluoroalkyl group having 1 to 8 C atoms, X denotes OR, Ac, OAr or OHet, Ac denotes a carboxyl group OC(O)R, also including salts of an aliphatic dicarboxylic acid having the formula Ib

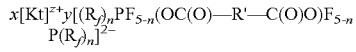

where
x denotes 2 and y denotes 1 if z denotes 1,
x denotes 1 and y denotes 1 if z denotes 2,
x denotes 2 and y denotes 3 if z denotes 3 and
x denotes 1 and y denotes 2 if z denotes 4 and R' denotes a single bond or an alkylene group having 1 to 4 C atoms, Ar denotes an aryl group having 6 to 12 C atoms, which may be unsubstituted or substituted by Hal, $NH_2$, $NAlk_2$, NHAlk, $NO_2$, CN, $SO_3H$ or OR, Alk denotes a straight-chain or branched alkyl group having 1 to 12 C atoms, Het denotes a heteroaryl group having 5 to 13 C atoms, which may be unsubstituted or substituted by Hal, $NH_2$, $NAlk_2$, NHAlk, $NO_2$, CN, $SO_3H$ or OR, R denotes H or a straight-chain or branched alkyl group having 1 to 20 C atoms, which may be partially substituted by Hal, $NH_2$, NHAlk, $NAlk_2$, OH, $NO_2$, CN or $SO_3H$, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —$SO_2$—, NH, —C(O)—, —O—C(O)— or —C(O)—O—
and Kt denotes a stabilised proton, a metal cation or an organic cation, Hal denotes F, Cl, Br or I, z denotes 1, 2, 3 or 4 and n denotes 1, 2 or 3, and/or tautomers or stereoisomers thereof, including mixtures thereof in all ratios or a preferred embodiment of a compound of the formula I of this type, as described above.

According to a preferred embodiment, the device of the invention is a dye or quantum dot solar cell, particularly preferably a dye solar cell.

Quantum dot solar cells are disclosed, for example, in U.S. Pat. No. 6,861,722. In dye solar cells, a dye is used in order to absorb the sunlight and convert it into electrical energy. There is no restriction per se regarding the type of dye so long as the LUMO value of the dye is slightly above the conduction band of the photoelectrode. Examples of dyes are disclosed in EP 0 986 079 A2, EP 1 180 774 A2 or EP 1 507 307 A1.

Preferred dyes are organic dyes, for example MK-1, MK-2 or MK-3 (the structure thereof is described in FIG. 1 of N. Koumura et al, J. Am. Chem. Soc. Vol 128, No. 44, 2006, 14256-14257), D102 (CAS No. 652145-28-3), D-149 (CAS No. 786643-20-7), D205 (CAS No. 936336-21-9), D358 (CAS No. 1207638-53-6), YD-2, as described in T. Bessho et al, Angew. Chem. Int. Ed. Vol 49, 37, 6646-6649, 2010, Y123 (CAS No. 1312465-92-1), bipyridineruthenium dyes, such as N3 (CAS No. 141460-19-7), N719 (CAS No. 207347-46-4), Z907 (CAS No. 502693-09-6), C101 (CAS No. 1048964-93-7), C106 (CAS No. 1152310-69-4), K19 (CAS No. 847665-45-6), SK-1 (CAS No. 906061-30-1), or terpyridineruthenium dyes, such as N749 (CAS No. 359415-47-7).

Particularly preferred dyes are the dyes Z907 or Z907Na, both of which are amphiphilic ruthenium sensitisers, or D205. The chemical name for Z907Na is NaRu(2,2'-bipyridine-4-carboxylic acid-4'-carboxylate)(4,4'-dinonyl-2,2'-bipyridine)(NCS)$_2$.

The structure of D205 is

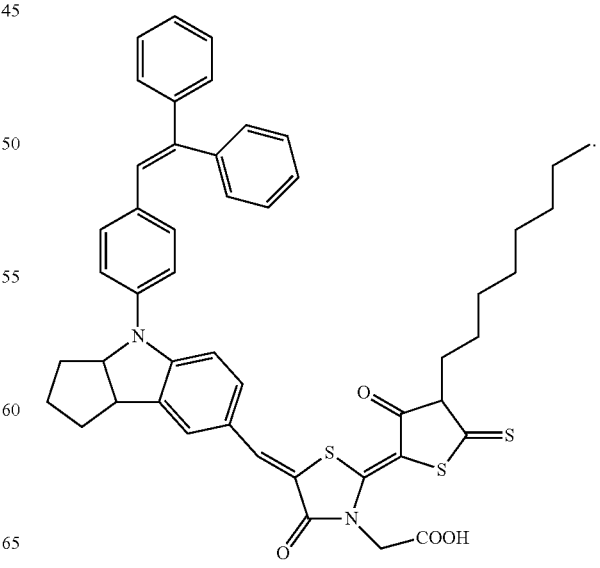

Very particular preference is given to the use of the dyes Z907 or Z907Na.

A dye-sensitised solar cell comprises, for example, a photoelectrode, a counterelectrode and, between the photoelectrode and the counterelectrode, an electrolyte formulation or a charge-transport material, where a sensitising dye is absorbed on the surface of the photoelectrode facing the counterelectrode.

According to a preferred embodiment of the device according to the invention, it comprises a semiconductor, the electrolyte formulation as described above and a counterelectrode.

According to a preferred embodiment of the invention, the semiconductor is based on material selected from the group Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. The semiconductor preferably comprises a mesoporous surface, which increases the surface, which is optionally covered with a dye and is in contact with the electrolyte. The semiconductor is preferably located on a glass support or plastic film or metal foil. The support is preferably conductive.

The device of the present invention preferably comprises a counterelectrode. For example, fluorine-doped tin oxide or tin-doped indium oxide on glass (FTO- or ITO-glass, respectively) coated with Pt, carbon of preferably conductive allotropes, polyaniline or poly(3,4-ethylenedioxythiophene) (PEDOT). Metal substrates, such as stainless steel or titanium sheet, are possible substrates beside glass.

The device of the present invention can be produced, like the corresponding device of the prior art, by simply replacing the electrolyte with the electrolyte formulation of the present invention. In the case of dye-sensitised solar cells, for example, device assembly is disclosed in numerous patent specifications, for example WO 91/16719 (Examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

The sensitised semiconducting material preferably serves as photoanode. The counterelectrode is preferably a cathode.

The present invention provides a process for the production of a photoelectric cell comprising the step of bringing the electrolyte formulation of the invention into contact with a surface of a semiconductor, where the surface is optionally coated with a sensitiser. The semiconductor is preferably selected from the materials given above, and the sensitiser is preferably selected from quantum dots and/or a dye as disclosed above, particularly preferably from a dye.

The electrolyte formulation can preferably simply be poured onto the semiconductor. It is preferably applied to the otherwise finished device, which already comprises a counterelectrode, by creating a vacuum in the internal lumen of the cell through a hole in the counterelectrode and adding the electrolyte formulation as disclosed in the reference from Wang et al., J. Phys. Chem. B 2003, 107, 14336.

The following working examples are intended to explain the invention without limiting it. The invention can be carried out correspondingly throughout the range claimed. Possible variants can also be derived starting from the examples. In particular, the features and conditions of the reactions described in the examples can also be applied to other reactions which are not shown in detail, but fall within the scope of protection of the claims.

EXAMPLES

The substances obtained are characterised by means of mass spectrometry, elemental analysis and NMR spectroscopy. NMR spectra are recorded using Avance III 300 spectrometers, from Bruker, Karlsruhe. Acetone-d6 is used in a capillary as lock substance. The referencing is carried out using external reference: TMS for $^1H$ and $^{13}C$ spectra; $CCl_3F$— for $^{19}F$ and 80% $H_3PO_4$— for $^{31}P$ spectra.

Example 1

Preparation of $[P(C_2F_5)_3F_2(dmap)]$

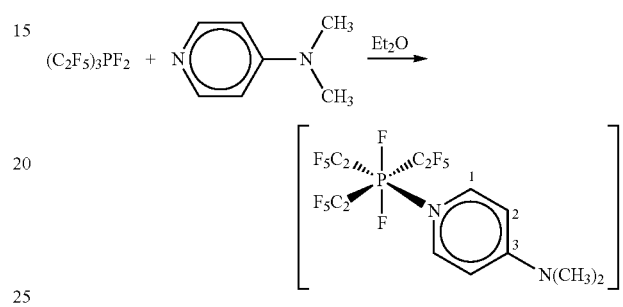

2.8 g (22.9 mmol) of 4-(dimethylamino)pyridine are initially introduced in 100 ml of diethyl ether, and 12.2 g (28.6 mmol) of $(C_2F_5)_3PF_2$ are slowly added. After stirring for 15 minutes, volatile constituents are removed in vacuo, leaving a colourless solid.

Yield (based on DMAP): 12.1 g (97%). Melting point: 150-153° C.

$^{31}P$-NMR spectroscopic data of $[P(C_2F_5)_3F_2(dmap)]$ in $Et_2O$

| δ, ppm | Multiplicity | J[Hz] | Assignment |
|---|---|---|---|
| −144.5 | t, quin, t | $^1J(PF) = 986$ | $[P(C_2F_5)_3F_2(dmap)]$ |
| | | $^2J(PF_{cis}) = 107$ | |
| | | $^2J(PF_{trans}) = 97$ | |

$^{19}F$-NMR spectroscopic data of $[P(C_2F_5)_3F_2(dmap)]$ in $Et_2O$

| δ, ppm | Multiplicity | J[Hz] | Assignment | Integral |
|---|---|---|---|---|
| −80.4 | m | — | trans-$CF_3$ | 1 |
| −81.6 | m | — | cis-$CF_3$ | 2 |
| −99.4 | d | $^1J(PF) = 986$ | PF | 0.6 |
| −111.5 | m (br) | — | cis-$CF_2$ | 1 |
| −115.3 | d, m | $^2J(PF) = 95$ | trans-$CF_2$ | 0.6 |

$^1H$-NMR spectroscopic data of $[P(C_2F_5)_3F_2(dmap)]$ in $CDCl_3$

| δ, ppm | Multiplicity | J[Hz] | Assignment | Integral |
|---|---|---|---|---|
| 3.2 | s | — | —$N(CH_3)_2$ | 3 |
| 6.7 | d | $^3J(HH) = 7$ | H2 | 1 |
| 8.4 | m (br) | — | H1 | 1 |

$^{13}$C-NMR spectroscopic data of [P(C$_2$F$_5$)$_3$F$_2$(dmap)] in CDCl$_3$

| δ, ppm | Multiplicity | J[Hz] | Assignment |
|---|---|---|---|
| 38.6 [a] | s | — | —N(CH$_3$)$_2$ |
| 105.9 [a] | s | — | C1 |
| 116.7 [b] | m | — | —CF$_2$CF$_3$ |
| 118.2 [b] | m | — | —CF$_2$CF$_3$ |
| 138.9 [a] | s | — | C2 |
| 156.1 [a] | s | — | C3 |

[a] {$^1$H}
[b] {$^{19}$F}

Elemental analysis data of [P(C$_2$F$_5$)$_3$F$_2$(dmap)]

|  | N | C | H |
|---|---|---|---|
| calculated | 5.11 | 28.48 | 1.84 |
| experimental | 4.91 | 28.63 | 1.67 |

Mass spectrometric data (EI, 20 eV)

| m/e | Rel. intensity [%] | Assignment |
|---|---|---|
| 407 | 12 | [P(C$_2$F$_5$)$_3$F(dmap)]$^+$ |
| 307 | 50 | [P(C$_2$F$_5$)$_2$F$_2$(dmap)]$^+$ |
| 207 | 15 | [P(C$_2$F$_5$)F$_3$(dmap)]$^+$ |
| 122 | 100 | [C$_7$H$_{10}$N$_2$]$^+$ |
| 69 | 6 | [CF$_3$]$^+$ |

Example 2

Preparation of [PPh$_4$][P(C$_2$F$_5$)$_3$F$_2$OH]

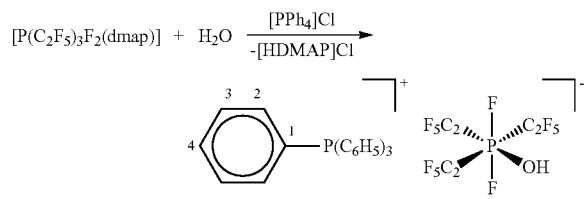

0.96 g (1.75 mmol) of [P(C$_2$F$_5$)$_3$F$_2$(dmap)] are initially introduced in ether, and excess water is added. After stirring for 30 minutes, 0.66 g (1.75 mmol) of [PPh$_4$]Cl, dissolved in 2 ml of water, are added, and the mixture is again stirred for 20 minutes. The aqueous phase is subsequently separated off, and the organic phase is extracted three times with water. The organic phase is dried in vacuo, leaving a colourless solid as residue. Yield (based on [P(C$_2$F$_5$)$_3$F$_2$(dmap)]: 1.29 g (94%). Melting point: 139° C.

$^{31}$P-NMR spectroscopic data of [PPh$_4$][P(C$_2$F$_5$)$_3$F$_2$OH] in CD$_3$CN

| δ, ppm | Multiplicity | J[Hz] | Assignment | Integral |
|---|---|---|---|---|
| 23.2 | s | — | [PPh$_4$][P(C$_2$F$_5$)$_3$F$_2$OH] | 1 |
| −148.3 | t, sept | $^1$J(PF) = 845<br>$^2$J(PF) = 86 | [PPh$_4$][P(C$_2$F$_5$)$_3$F$_2$OH] |  |

$^{19}$F-NMR spectroscopic data of [PPh$_4$][P(C$_2$F$_5$)$_3$F$_2$OH] in CD$_3$CN

| δ, ppm | Multiplicity | J[Hz] | Assignment | Integral |
|---|---|---|---|---|
| −80.1 | m | — | trans-CF$_3$ | 1 |
| −81.2 | m | — | cis-CF$_3$ | 2.2 |
| −86.6 | d, m | $^1$J(PF) = 846 | PF | 0.3 |
| −114.1 | d | $^2$J(PF) = 86 | cis-, trans-CF$_2$ | 2.5 |

$^1$H-NMR spectroscopic data of [PPh$_4$][P(C$_2$F$_5$)$_3$F$_2$OH] in CD$_3$CN

| δ, ppm | Multiplicity | J[Hz] | Assignment | Integral |
|---|---|---|---|---|
| 5.1 | t, d | $^3$J(FH) = 14<br>$^2$J(PH) = 3 | [P(C$_2$F$_5$)$_3$F$_2$OH]$^-$ | 1 |
| 7.8-8.1 | m | — | [PPh$_4$]$^+$ | 22 |

$^{13}$C-NMR spectroscopic data of [PPh$_4$][P(C$_2$F$_5$)$_3$F$_2$OH] in CD$_3$CN

| δ, ppm | Multiplicity | J[Hz] | Assignment |
|---|---|---|---|
| 118.5 [a] | d | $^1$J(PC) = 90 | C1 |
| 119.1 [b] | m | — | —CF$_2$CF$_3$ |
| 120.7 [b] | m | — | —CF$_2$CF$_3$ |
| 130.3 [a] | d | $^2$J(PC) = 13 | C2 |
| 134.7 [a] | d | $^3$J(PC) = 10 | C3 |
| 135.4 [a] | d | $^4$J(PC) = 3 | C4 |

[a] {$^1$H}
[b] {$^{19}$F}

Elemental analysis data of [PPh$_4$][P(C$_2$F$_5$)$_3$F$_2$OH]

|  | C | H |
|---|---|---|
| calculated | 46.05 | 2.71 |
| experimental | 46.40 | 2.79 |

Mass spectrometric data (ESI, negative scan mode)

| Signal | Rel. intensity [%] | Assignment |
|---|---|---|
| 443.18 | 100 | [P(C$_2$F$_5$)$_3$F$_2$OH]$^-$ |
| 323.15 | 41 | [P(C$_2$F$_5$)$_2$F$_2$O]$^-$ |

Example 3

Preparation of [HDMAP][P(C$_2$F$_5$)$_3$F$_2$OC(O)CH$_3$]

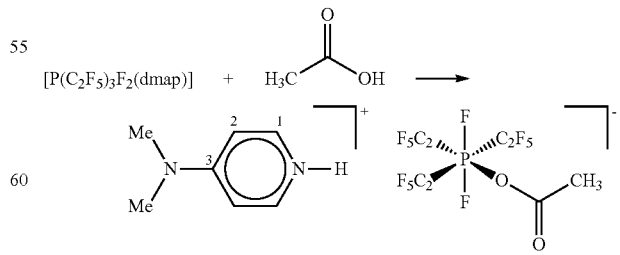

0.52 g (0.96 mmol) of [P(C$_2$F$_5$)$_3$F$_2$(dmap)] are initially introduced in dichloromethane. 0.19 g (3.17 mmol) of acetic acid are added at room temperature, and the reaction mixture is stirred for 3 hours. Volatile constituents are subsequently removed in vacuo, leaving a colourless solid. Yield (based on [P(C$_2$F$_5$)$_3$F$_2$(dmap)]): 0.54 g (93%)

$^{31}$P-NMR spectroscopic data of [HDMAP][P(C$_2$F$_5$)$_3$F$_2$OC(O)CH$_3$] in CD$_3$CN

| δ, ppm | Multiplicity | J[Hz] | Assignment |
|---|---|---|---|
| −146.3 | t, quin, t | $^1$J(PF) = 915<br>$^2$J(PF$_{cis}$) = 103<br>$^2$J(PF$_{trans}$) = 84 | [P(C$_2$F$_5$)$_3$F$_2$OC(O)CH$_3$]$^−$ |

$^{19}$F-NMR spectroscopic data of [HDMAP][P(C$_2$F$_5$)$_3$F$_2$OC(O)CH$_3$] in CD$_3$CN

| δ, ppm | Multiplicity | J[Hz] | Assignment | Integral |
|---|---|---|---|---|
| −80.2 | m | — | trans-CF$_3$ | 1 |
| −81.8 | m | — | cis-CF$_3$ | 2 |
| −86.9 | d, m | $^1$J(PF) = 923 | PF | 0.6 |
| −115.3 | d, m | $^2$J(PF) = 85 | trans-CF$_2$ | — |
| −116.0 | d, m | $^2$J(PF) = 103 | cis-CF$_2$ | — |

$^1$H-NMR spectroscopic data of [HDMAP][P(C$_2$F$_5$)$_3$F$_2$OC(O)CH$_3$] in CD$_3$CN

| δ, ppm | Multiplicity | J[Hz] | Assignment | Integral |
|---|---|---|---|---|
| 1.9 | s | — | —OC(O)CH$_3$ | 1.6 |
| 3.2 | s | — | —N(CH$_3$)$_2$ | 3 |
| 6.9 | d | $^3$J(HH) = 7 | H1 | 1 |
| 7.9 | d | $^3$J(HH) = 7 | H2 | 1 |

$^{13}$C-NMR spectroscopic data of [HDMAP][P(C$_2$F$_5$)$_3$F$_2$OC(O)CH$_3$] in CD$_3$CN

| δ, ppm | Multiplicity | J[Hz] | Assignment |
|---|---|---|---|
| 23.3 [a] | s | — | —OC(O)CH$_3$ |
| 39.6 [a] | s | — | —N(CH$_3$)$_2$ |
| 107.1 [a] | s | — | C1 |
| 116.7 [b] | m | — | —CF$_2$CF$_3$ |
| 120.0 [b] | m | — | —CF$_2$CF$_3$ |
| 138.6 [a] | s | — | C2 |
| 157.7 [a] | s | — | C3 |
| 166.3 [a] | d | $^2$J(PC) = 18 | —OC(O)CH$_3$ |

[a] {$^1$H}
[b] {$^{19}$F}

Example 4

Preparation of [HDMAP][P(C$_2$F$_5$)$_3$F$_2$OPh]

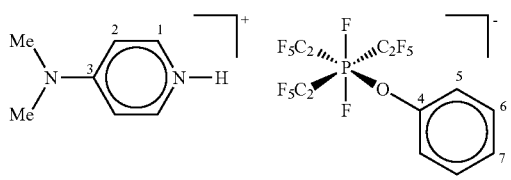

0.52 g (0.95 mmol) of [P(C$_2$F$_5$)$_3$F$_2$(dmap)] are initially introduced in diethyl ether. 0.13 g (1.34 mmol) of phenol are added at room temperature, and the reaction mixture is stirred for 12 hours. Two phases form. The solvent is removed in vacuo, leaving a clear, colourless liquid.

$^{31}$P-NMR spectroscopic data of [HDMAP][P(C$_2$F$_5$)$_3$F$_2$OPh] in CD$_3$CN

| δ, ppm | Multiplicity | J[Hz] | Assignment |
|---|---|---|---|
| −147.5 | t, quin, t | $^1$J(PF) = 893<br>$^2$J(PF$_{cis}$) = 98<br>$^2$J(PF$_{trans}$) = 84 | [P(C$_2$F$_5$)$_3$F$_2$OPh]$^−$ |

$^{19}$F-NMR spectroscopic data of [HDMAP][P(C$_2$F$_5$)$_3$F$_2$OPh] in CD$_3$CN

| δ, ppm | Multiplicity | J[Hz] | Assignment | Integral |
|---|---|---|---|---|
| −79.4 | m | — | trans-CF$_3$ | — |
| −80.5 | m | — | cis-CF$_3$ | — |
| −85.5 | d, m | $^1$J(PF) = 896 | PF | — |
| −111.5 | d, m | $^2$J(PF) = 97 | cis-CF$_2$ | — |
| −112.7 | d, m | $^2$J(PF) = 79 | trans-CF$_2$ | — |

$^1$H-NMR spectroscopic data of [HDMAP][P(C$_2$F$_5$)$_3$F$_2$OPh] in CD$_3$CN

| δ, ppm | Multiplicity | J[Hz] | Assignment | Integral |
|---|---|---|---|---|
| 3.4 | s | — | —N(CH$_3$)$_2$ | 3 |
| 6.7 | d | $^3$J(HH) = 7 | H1 | 1 |
| 7.1 | m | — | —OC$_6$H$_5$ | 2.2 |
| 8.3 | d | $^3$J(HH) = 7 | H2 | 1 |

$^{13}$C-NMR spectroscopic data of [HDMAP][P(C$_2$F$_5$)$_3$F$_2$OPh] in CD$_3$CN

| δ, ppm | Multiplicity | J[Hz] | Assignment |
|---|---|---|---|
| 39.7 [a] | s | — | —N(CH$_3$)$_2$ |
| 106.9 [a] | s | — | C1 |
| 115.2 [a] | s | — | C5 |
| 118.1 [b] | m | — | —CF$_2$CF$_3$ |
| 119.7 [b] | m | — | —CF$_2$CF$_3$ |
| 120.4 [a] | s | — | C6/7 |
| 128.9 [a] | s | — | C6/7 |
| 138.8 [a] | s | — | C2 |
| 157.0 [a] | s | — | C4 |
| 157.6 [a] | s | — | C3 |

[a] {$^1$H}
[b] {$^{19}$F}

Example 5

Preparation of [HDMAP]$_2$[{P(C$_2$F$_5$)$_3$F$_2$O}$_2$C$_6$H$_4$]

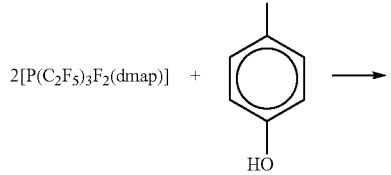

-continued

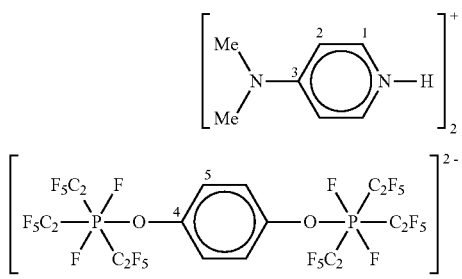

1.11 g (2 mmol) of [P(C$_2$F$_5$)$_3$F$_2$(dmap)] are initially introduced in diethyl ether. 0.11 g (1 mmol) of hydroquinone are added at room temperature, and the reaction mixture is stirred for 4 hours. Volatile constituents are subsequently removed in vacuo, leaving a colourless solid. Yield (based on hydroquinone): 0.85 g (78%).

$^{31}$P-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment |
|---|---|---|---|
| −148.0 | t, quin, t | $^1$J(PF) = 882 | [{P(C$_2$F$_5$)$_3$F$_2$O}$_2$C$_6$H$_4$]$^{2-}$ |
|  |  | $^2$J(PF$_{cis}$) = 96 |  |
|  |  | $^2$J(PF$_{trans}$) = 78 |  |

$^{19}$F-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment | Integral |
|---|---|---|---|---|
| −80.4 | m | — | trans-CF$_3$ | 1 |
| −81.6 | m | — | cis-CF$_3$ | 2 |
| −86.9 | d, m | $^1$J(PF) = 881 | PF | 0.6 |
| −112.9 | d, m | $^2$J(PF) = 98 | cis-CF$_2$ | 1.3 |
| −113.9 | d, m | $^2$J(PF) = 80 | trans-CF$_2$ | 0.7 |

$^1$H-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment | Integral |
|---|---|---|---|---|
| 3.1 | s | — | —N(CH$_3$)$_2$ | 3 |
| 6.8 | m | — | H5/6 | 0.5 |
| 6.8 | d | $^3$J(HH) = 8 | H1 | 1 |
| 7.9 | d | $^3$J(HH) = 8 | H2 | 1 |

Elemental analysis data of [HDMAP]$_2$[{P(C$_2$F$_5$)$_3$F$_2$O}$_2$C$_6$H$_4$]

|  | N | C | H |
|---|---|---|---|
| calculated | 4.67 | 32.07 | 1.51 |
| experimental | 4.73 | 32.40 | 2.26 |

Example 6

Preparation of [HDMAP][P(C$_2$F$_5$)$_3$F$_2$OEt]

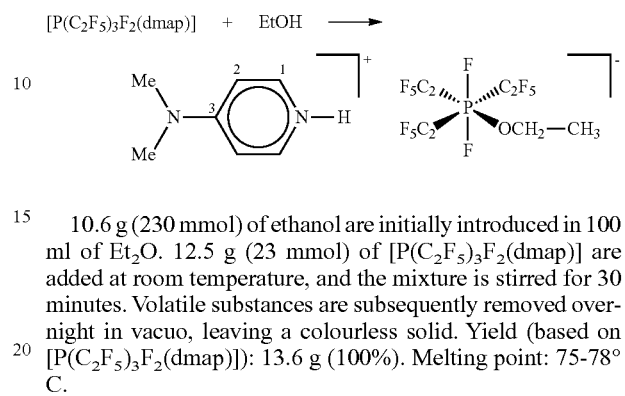

10.6 g (230 mmol) of ethanol are initially introduced in 100 ml of Et$_2$O. 12.5 g (23 mmol) of [P(C$_2$F$_5$)$_3$F$_2$(dmap)] are added at room temperature, and the mixture is stirred for 30 minutes. Volatile substances are subsequently removed overnight in vacuo, leaving a colourless solid. Yield (based on [P(C$_2$F$_5$)$_3$F$_2$(dmap)]): 13.6 g (100%). Melting point: 75-78° C.

$^{31}$P-NMR spectroscopic data of [HDMAP][P(C$_2$F$_5$)$_3$F$_2$OEt] in CD$_3$CN

| δ, ppm | Multiplicity | J[Hz] | Assignment |
|---|---|---|---|
| −149.4 | t, sept | $^1$J(PF) = 869 | [P(C$_2$F$_5$)$_3$F$_2$OC$_2$H$_5$]$^-$ |
|  |  | $^2$J(PF) = 88 |  |

$^{19}$F-NMR spectroscopic data of [HDMAP][P(C$_2$F$_5$)$_3$F$_2$OEt] in CD$_3$CN

| δ, ppm | Multiplicity | J[Hz] | Assignment | Integral |
|---|---|---|---|---|
| −80.6 | m | — | trans-CF$_3$ | 1 |
| −81.8 | m | — | cis-CF$_3$ | 2 |
| −94.5 | d | $^1$J(PF) = 869 | PF | 0.6 |
| −113.5 | d, m | $^2$J(PF) = 83 | trans-CF$_2$ | 0.6 |
| −114.4 | d, m | $^2$J(PF) = 86 | cis-CF$_2$ | 1.3 |

$^1$H-NMR spectroscopic data of [HDMAP][P(C$_2$F$_5$)$_3$F$_2$OEt] in CD$_3$CN

| δ, ppm | Multiplicity | J[Hz] | Assignment | Integral |
|---|---|---|---|---|
| 1.1 | t, d | $^3$J(HH) = 7 | —OCH$_2$CH$_3$ | 1.4 |
|  |  | $^4$J(PH) = 1 |  |  |
| 3.2 | s | — | —N(CH$_3$)$_2$ | 3 |
| 4.0 | pseudo-quin | $^3$J(PH) = 7 | —OCH$_2$CH$_3$ | 0.9 |
|  |  | $^3$J(HH) = 7 |  |  |
| 5.3 | s | — | —NH$^+$ | 1 |
| 6.8 | d | $^3$J(HH) = 7 | H1 | 1 |
| 8.0 | d | $^3$J(HH) = 7 | H2 | 1 |

$^{13}$C-NMR spectroscopic data of [HDMAP][P(C$_2$F$_5$)$_3$F$_2$OEt] in CD$_3$CN

| δ, ppm | Multiplicity | J[Hz] | Assignment |
|---|---|---|---|
| 16.0 $^a$ | d | $^3$J(CP) = 10 | —OCH$_2$CH$_3$ |
| 39.6 $^a$ | s | — | (CH$_3$)$_2$N— |
| 61.8 $^a$ | m | — | —OCH$_2$CH$_3$ |
| 107.1 $^a$ | s | — | C1 |
| 118.8 $^b$ | m | — | —CF$_2$CF$_3$ |
| 122.5 $^b$ | m | — | —CF$_2$CF$_3$ |

-continued

| δ, ppm | Multiplicity | J[Hz] | Assignment |
|---|---|---|---|
| 138.5 [a] | s | — | C2 |
| 157.9 [a] | s | — | C3 |

[a] {$^1$H}
[b] {$^{19}$F}

Elemental analysis data of [HDMAP][P(C$_2$F$_5$)$_3$F$_2$OEt]

| | N | C | H |
|---|---|---|---|
| calculated | 4.71 | 30.32 | 2.71 |
| experimental | 4.74 | 30.32 | 2.69 |

Mass spectrometric data (ESI, negative scan mode)

| Signal | Rel. intensity [%] | Assignment |
|---|---|---|
| 965.04 | 9 | — |
| 471.16 | 100 | [P(C$_2$F$_5$)$_3$F$_2$OC$_2$H$_5$]$^-$ |
| 445.11 | 21 | [P(C$_2$F$_5$)$_3$F$_3$]$^-$ |

Example 7

Preparation of [HDMAP][P(C$_2$F$_5$)$_3$F$_2$OCH$_2$CF$_3$]

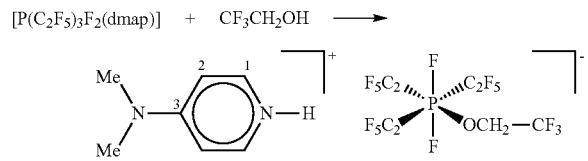

2.5 g (4.5 mmol) of [P(C$_2$F$_5$)$_3$F$_2$(dmap)] are initially introduced in diethyl ether. 0.9 g (9.0 mmol) of trifluoroethanol are added at room temperature, and the reaction mixture is stirred for 12 hours. Volatile constituents are subsequently removed in vacuo, leaving a colourless solid. Yield (based on [P(C$_2$F$_5$)$_3$F$_2$(dmap)]): 2.8 g (95%). Melting point: 91-93° C.

$^{31}$P-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment |
|---|---|---|---|
| −149.9 | t, sept | $^1$J(PF) = 886<br>$^2$J(PF) = 88 | [P(C$_2$F$_5$)$_3$F$_2$OCH$_2$CF$_3$]$^-$ |

$^{19}$F-NMR spectroscopic data of [HDMAP][(C$_2$F$_5$)$_3$PF$_2$OCH$_2$CF$_3$] in CD$_3$CN

| δ, ppm | Multiplicity | J[Hz] | Assignment | Integral |
|---|---|---|---|---|
| −75.4 | s | — | [P(C$_2$F$_5$)$_3$F$_2$OCH$_2$CF$_3$]$^-$ | 1 |
| −79.6 | m | — | trans-CF$_3$ | 1 |
| −80.8 | m | — | cis-CF$_3$ | 2 |
| −93.8 | d, m | $^1$J(PF) = 883 | PF | 0.5 |
| −112.2 | d, m | — | trans-, cis-CF$_3$ | 2.2 |

$^1$H-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment | Integral |
|---|---|---|---|---|
| 3.2 | s | — | —N(CH$_3$)$_2$ | 3 |
| 4.4 | quar, d | $^3$J(FH) = 9<br>$^3$J(PH) = 4 | —OCH$_2$CF$_3$ | 1 |
| 6.8 | d | $^3$J(HH) = 7 | H1 | 1 |
| 8.0 | d | — | H2 | 1 |

$^{13}$C-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment |
|---|---|---|---|
| 39.6 [a] | s | — | —N(CH$_3$)$_2$ |
| 64.1 [a] | m | — | —OCH$_2$CF$_3$ |
| 106.9 [a] | s | — | C1 |
| 118.8 [b] | m | — | —CF$_2$CF$_3$ |
| 120.4 [b] | m | — | —CF$_2$CF$_3$ |
| 124.5 [b] | m | — | —OCH$_2$CF$_3$ |
| 138.9 [a] | s | — | C2 |
| 157.7 [a] | s | — | C3 |

[a] {$^1$H}
[b] {$^{19}$F}

Elemental analysis data of [HDMAP][P(C$_2$F$_5$)$_3$F$_2$OCH$_2$CF$_3$]

| | N | C | H |
|---|---|---|---|
| calculated | 4.32 | 27.79 | 2.02 |
| experimental | 4.47 | 28.10 | 1.64 |

Mass spectrometric data (ESI, negative scan mode)

| Signal | Rel. intensity [%] | Assignment |
|---|---|---|
| 1088.97 | 13 | — |
| 525.15 | 100 | [P(C$_2$F$_5$)$_3$F$_2$OCH$_2$CF$_3$]$^-$ |

Example 8

Preparation of [HDMAP][P(C$_2$F$_5$)$_3$F$_2$ODec]

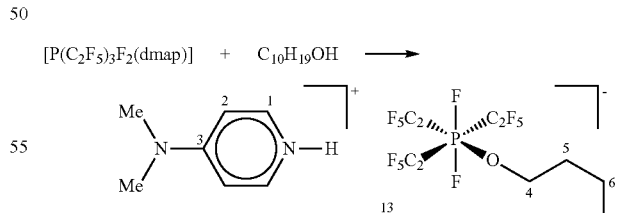

0.69 g (1.25 mmol) of [P(C$_2$F$_5$)$_3$F$_2$(dmap)] are dissolved in Et$_2$O. 0.20 g (1.25 mmol) of 9-decen-1-ol are added at room temperature, and the mixture is stirred for 1.5 hours. The reaction mixture is subsequently dried in vacuo, leaving a clear viscous liquid. Yield (based on [P(C$_2$F$_5$)$_3$F$_2$(dmap)]): 0.88 g (99%). Melting point: <20° C.

$^{31}$P-NMR spectroscopic data of [HDMAP][P(C$_2$F$_5$)$_3$F$_2$ODec] in CDCl$_3$

| δ, ppm | Multiplicity | J[Hz] | Assignment |
|---|---|---|---|
| −147.2 | t, sept | $^1$J(PF) = 873<br>$^2$J(PF) = 88 | [P(C$_2$F$_5$)$_3$F$_2$OC$_{10}$H$_{19}$]$^−$ |

$^{19}$F-NMR spectroscopic data of [HDMAP][P(C$_2$F$_5$)$_3$F$_2$ODec] in CDCl$_3$

| δ, ppm | Multiplicity | J[Hz] | Assignment | Integral |
|---|---|---|---|---|
| −79.7 | m | — | trans-CF$_3$ | 1 |
| −81.0 | m | — | cis-CF$_3$ | 2.1 |
| −94.9 | d, m | $^1$J(PF) = 876 | PF | 0.5 |
| −113.0 | d, m | — | cis-, trans-CF$_2$ | 2.1 |

$^1$H-NMR spectroscopic data of [HDMAP][P(C$_2$F$_5$)$_3$F$_2$ODec] in CDCl$_3$

| δ, ppm | Multiplicity | J[Hz] | Assignment | Integral |
|---|---|---|---|---|
| 1.2-1.6 | m | — | H6-H10 | 5.7 |
| 1.5 | t | $^3$J(HH) = 7 | H5 | — |
| 2.0 | quin | $^3$J(HH) = 7 | H11 | 1 |
| 3.2 | s | — | —N(CH$_3$)$_2$ | 3 |
| 3.7 | t | $^3$J(HH) = 7 | H4 | 0.6 |
| 4.9-5.0 | m | — | H13 | 0.9 |
| 5.8 | m | — | H12 | 0.5 |
| 6.7 | d | $^3$J(HH) = 7 | H1 | 1 |
| 7.8 | d | $^3$J(HH) = 7 | H2 | 1 |

$^{13}$C{$^1$H}-NMR spectroscopic data of [HDMAP][P(C$_2$F$_5$)$_3$F$_2$ODec] in CDCl$_3$

| δ, ppm | Multiplicity | J[Hz] | Assignment |
|---|---|---|---|
| 25.7; 28.9;<br>29.0; 29.3;<br>29.4 | s | — | C6-C10 |
| 32.8 | s | — | C5 |
| 33.8 | s | — | C11 |
| 40.0 | s | — | —N(CH$_3$)$_2$ |
| 63.2 | s | — | C4 |
| 107.0 | s | — | C1 |
| 114.1 | s | — | C13 |
| 138.5 | s | — | C2 |
| 139.3 | s | — | C12 |
| 157.4 | s | — | C3 |

Example 9

Preparation of [BMMIM][P(C$_2$F$_5$)$_3$F$_2$OEt]

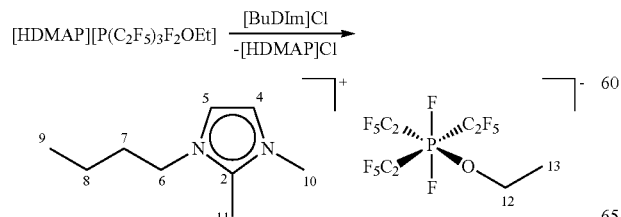

5.3 g (9 mmol) of [HDMAP][P(C$_2$F$_5$)$_3$F$_2$OEt] are dissolved in 50 ml of dichloromethane, and 1.7 g (9 mmol) of 1-butyl-2,3-dimethylimidazolium chloride, dissolved in 5 ml of dichloromethane, are added. The reaction mixture is stirred at room temperature for 1.5 hours and subsequently extracted three times with water. Volatile constituents of the organic phase are removed in vacuo, leaving a colourless liquid. Yield (based on 1-butyl-2,3-dimethylimidazolium chloride): 4.9 g (87%).

Analytical data of [BuDIm][P(C$_2$F$_5$)$_3$F$_2$OEt]

| | |
|---|---|
| Glass transition [° C.] | −57 |
| Decomposition [° C.] | 120 |
| H$_2$O content [ppm] | 13.1 |
| Cl$^−$ content [ppm] | 87.5 |
| F$^−$ content [ppm] | 1202 |

$^{31}$P-NMR spectroscopic data of [BuDIm][P(C$_2$F$_5$)$_3$F$_2$OEt] in CD$_3$CN

| δ, ppm | Multiplicity | J[Hz] | Assignment |
|---|---|---|---|
| −149.5 | t, sept | $^1$J(PF) = 866<br>$^2$J(PF) = 84 | [P(C$_2$F$_5$)$_3$F$_2$OEt]$^−$ |

$^{19}$F-NMR spectroscopic data of [BuDIm][P(C$_2$F$_5$)$_3$F$_2$OEt] in CD$_3$CN

| δ, ppm | Multiplicity | J[Hz] | Assignment | Integral |
|---|---|---|---|---|
| −80.1 | m | — | trans-CF$_3$ | 3 |
| −81.3 | m | — | cis-CF$_3$ | 6 |
| −93.9 | d, m | $^1$J(PF) = 870 | PF | 2 |
| −113.3 | d, m | $^2$J(PF) = 84 | trans-CF$_2$ | 2 |
| −116.9 | d, m | $^2$J(PF) = 86 | cis-CF$_2$ | 4 |

$^1$H-NMR spectroscopic data of [BuDIm][P(C$_2$F$_5$)$_3$F$_2$OEt] in CD$_3$CN

| δ, ppm | Multiplicity | J[Hz] | Assignment | Integral |
|---|---|---|---|---|
| 0.9 | t | $^3$J(HH) = 7 | H9/H13 | 3 |
| 1.0 | t | $^3$J(HH) = 7 | H13/H9 | 3 |
| 1.3 | sext | $^3$J(HH) = 8 | H8 | 2 |
| 1.7 | quin | $^3$J(HH) = 7 | H7 | 2 |
| 2.5 | s | — | H11 | 3 |
| 3.7 | s | — | H10 | 3 |
| 3.9 | m | — | H6, H12 | 4 |
| 7.2 | m | — | H4, H5 | 2 |

$^{13}$C{$^1$H}-NMR spectroscopic data of [BuDIm][P(C$_2$F$_5$)$_3$F$_2$OEt] in CD$_3$CN

| δ, ppm | Multiplicity | J[Hz] | Assignment |
|---|---|---|---|
| 9.0 | s | — | C11 |
| 12.7 | s | — | C9 |
| 16.0 | s | — | C13 |
| 19.1 | s | — | C8 |
| 31.2 | s | — | C7 |
| 34.7 | s | — | C10 |
| 48.0 | s | — | C6 |
| 61.8 | s | — | C12 |
| 120.8 | s | — | C4/5 |
| 122.2 | s | — | C4/5 |
| 144.3 | s | — | C2 |

Example 10

Preparation of [BMMIM][P(C$_2$F$_5$)$_3$F$_2$OCH$_2$CF$_3$]

[HDMAP][P(C$_2$F$_5$)$_3$F$_2$OCH$_2$CF$_3$] $\xrightarrow[-[\text{HDMAP}]\text{Cl}]{[\text{BuDIm}]\text{Cl}}$

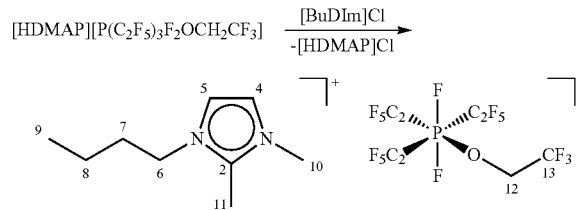

4.7 g (7.3 mmol) of [HDMAP][P(C$_2$F$_5$)$_3$F$_2$OCH$_2$CF$_3$] are dissolved in 50 ml of dichloromethane, and 1.4 g (7.4 mmol) of 1-butyl-2,3-dimethylimidazolium chloride, dissolved in 3 ml of dichloromethane, are added. The reaction mixture is stirred at room temperature for 1 hour and subsequently extracted three times with water. Volatile constituents of the organic phase are removed in vacuo, leaving a colourless liquid. Yield (based on 1-butyl-2,3-dimethylimidazolium chloride): 4.5 g (91%).

TABLE

Analytical data of [BuDIm][P(C$_2$F$_5$)$_3$F$_2$OCH$_2$CF$_3$]

| | |
|---|---|
| Glass transition [° C.] | −58 |
| Decomposition [° C.] | 212 |
| H$_2$O content [ppm] | 24.4 |
| Cl$^-$ content [ppm] | <5 |
| F$^-$ content [ppm] | 74 |

$^{31}$P-NMR spectroscopic data of [BuDIm][P(C$_2$F$_5$)$_3$F$_2$OCH$_2$CF$_3$] in CD$_3$CN

| δ, ppm | Multiplicity | J[Hz] | Assignment |
|---|---|---|---|
| −149.9 | t, sept | $^1$J(PF) = 885<br>$^2$J(PF) = 85 | [P(C$_2$F$_5$)$_3$F$_2$OCH$_2$CF$_3$]$^-$ |

$^{19}$F-NMR spectroscopic data of [BuDIm][P(C$_2$F$_5$)$_3$F$_2$OCH$_2$CF$_3$] in CD$_3$CN

| δ, ppm | Multiplicity | J[Hz] | Assignment | Integral |
|---|---|---|---|---|
| −75.9 | s | — | —OCH$_2$CF$_3$ | 3 |
| −80.3 | m | — | trans-CF$_3$ | 3 |
| −81.7 | m | — | cis-CF$_3$ | 6 |
| −94.5 | d, m | $^1$J(PF) = 884 | PF | 2 |
| −113.4 | m | — | cis-, trans-CF$_2$ | 6 |

$^1$H-NMR spectroscopic data of [BuDIm][P(C$_2$F$_5$)$_3$F$_2$OCH$_2$CF$_3$] in CD$_3$CN

| δ, ppm | Multiplicity | J[Hz] | Assignment | Integral |
|---|---|---|---|---|
| 0.9 | t | $^3$J(HH) = 7 | H9 | 3 |
| 1.3 | sext | $^3$J(HH) = 8 | H8 | 2 |
| 1.7 | quin | $^3$J(HH) = 7 | H7 | 2 |
| 2.5 | s | — | H11 | 3 |
| 3.7 | s | — | H10 | 3 |
| 4.0 | t | $^3$J(HH) = 7 | H6 | 2 |
| 4.4 | m | — | H12 | 2 |
| 7.2 | m | — | H4, H5 | 2 |

$^{13}$C{1H}-NMR spectroscopic data of [BuDIm][P(C$_2$F$_5$)$_3$F$_2$OCH$_2$CF$_3$] in CD$_3$CN

| δ, ppm | Multiplicity | J[Hz] | Assignment |
|---|---|---|---|
| 9.0 | s | — | C11 |
| 12.7 | s | — | C9 |
| 19.1 | s | — | C8 |
| 31.2 | s | — | C7 |
| 34.7 | s | — | C10 |
| 48.0 | s | — | C6 |
| 64.2 | m | — | C12 |
| 120.8 | s | — | C4/5 |
| 122.3 | s | — | C4/5 |
| 124.5 | m | — | C13 |
| 144.8 | s | — | C2 |

Example 11

Preparation of [HDMAP][P(C$_2$F$_5$)$_3$F$_2$OC$_2$H$_4$OH]

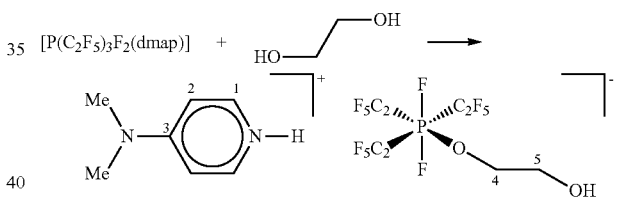

0.60 g (1.1 mmol) of [P(C$_2$F$_5$)$_3$F$_2$(dmap)] are initially introduced in diethyl ether. 0.10 g (1.6 mmol) of ethylene glycol are added at room temperature, and the reaction mixture is stirred for 24 hours. Volatile constituents are subsequently removed in vacuo, leaving a colourless solid. Yield (based on [P(C$_2$F$_5$)$_3$F$_2$(dmap)]): 0.61 g (89%). Melting point: 88° C. (softening of the sample), 91° C. decomposition.

$^{31}$P-NMR spectroscopic data of [HDMAP][P(C$_2$F$_5$)$_3$F$_2$OC$_2$H$_4$OH]

| δ, ppm | Multiplicity | J[Hz] | Assignment |
|---|---|---|---|
| −149.2 | t, sept | $^1$J(PF) = 871<br>$^2$J(PF) = 86 | [P(C$_2$F$_5$)$_3$F$_2$OC$_2$H$_4$OH]$^-$ |

$^{19}$F-NMR spectroscopic data of [HDMAP][P(C$_2$F$_5$)$_3$F$_2$OC$_2$H$_4$OH]

| δ, ppm | Multiplicity | J[Hz] | Assignment | Integral |
|---|---|---|---|---|
| −79.3 | m | — | trans-CF$_3$ | 1 |
| −80.4 | m | — | cis-CF$_3$ | 1.8 |

-continued

| δ, ppm | Multiplicity | J[Hz] | Assignment | Integral |
|---|---|---|---|---|
| −93.2 | d, m | $^1J(PF) = 873$ | PF | 0.3 |
| −112.6 | d, m | $^2J(PF) = 83$ | trans-, cis-$CF_2$ | 1.8 |

$^1$H-NMR spectroscopic data of [HDMAP] $[P(C_2F_5)_3F_2OC_2H_4OH]$

| δ, ppm | Multiplicity | J[Hz] | Assignment | Integral |
|---|---|---|---|---|
| 3.2 | s | — | $N(CH_3)_2$ | 3 |
| 3.5 | t | $^3J(HH) = 4$ | H5 | 0.8 |
| 4.0 | pseudo-quar | $^3J(HH) = 4$ $^3J(PH) = 4$ | H4 | 0.6 |
| 6.8 | d | $^3J(HH) = 8$ | H1 | 1 |
| 8.0 | d | $^3J(HH) = 8$ | H2 | 1 |

$^{13}$C-NMR spectroscopic data of [HDMAP] $[P(C_2F_5)_3F_2OC_2H_4OH]$

| δ, ppm | Multiplicity | J[Hz] | Assignment |
|---|---|---|---|
| 39.6 [a] | s | — | —$N(CH_3)_2$ |
| 62.1 [a] | d | $^2J(PC) = 9$ | C4 |
| 67.8 [a] | s | — | C5 |
| 106.8 [a] | s | — | C1 |
| 116.7 [b] | m | — | —$CF_2CF_3$ |
| 120.6 [b] | m | — | —$CF_2CF_3$ |
| 138.6 [a] | s | — | C2 |
| 157.6 [a] | s | — | C3 |

[a] $\{^1H\}$ [b] $\{^{19}F\}$

Elemental analysis data of [HDMAP] $[P(C_2F_5)_3F_2OC_2H_4OH]$

| | N | C | H |
|---|---|---|---|
| calculated | 4.59 | 29.52 | 2.64 |
| experimental | 4.62 | 29.54 | 2.28 |

Example 12

Preparation of $[P(C_2F_5)_3F_2(dmf)]$

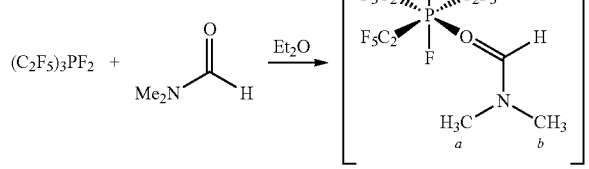

0.12 g (1.7 mmol) of DMF are initially introduced in about 15 ml of diethyl ether, and 1.02 g (2.4 mmol) of $(C_2F_5)_3PF_2$ are added. The reaction mixture is stirred at room temperature for 45 minutes. The solvent and excess $(C_2F_5)_3PF_2$ are subsequently removed in vacuo, leaving a colourless solid. Yield (based on DMF): 0.84 g (99%).

$^{31}$P-NMR spectroscopic data of $[P(C_2F_5)_3F_2(dmf)]$ in DMF

| δ, ppm | Multiplicity | J[Hz] | Assignment |
|---|---|---|---|
| −142.1 | t, t, quin | $^1J(PF) = 960$ $^2J(PF_{trans}) = 87$ $^2J(PF_{cis}) = 103$ | $[P(C_2F_5)_3F_2(dmf)]$ |

$^{19}$F-NMR spectroscopic data of $[P(C_2F_5)_3F_2(dmf)]$ in DMF

| δ, ppm | Multiplicity | J[Hz] | Assignment | Integral |
|---|---|---|---|---|
| −81.4 | m | — | trans-$CF_3$ | 1 |
| −82.4 | m | — | cis-$CF_3$ | 2 |
| −92.6 | d, m (br) | $^1J(PF) = 947$ | PF | 0.3 |
| −113.8 | m (br) | — | cis-$CF_2$ | 1 |
| −116.4 | d | $^2J(PF) = 88$ | trans-$CF_2$ | 0.6 |

$^1$H-NMR spectroscopic data of $[P(C_2F_5)_3F_2(dmf)]$ in DMF

| δ, ppm | Multiplicity | J[Hz] | Assignment | Integral |
|---|---|---|---|---|
| 2.7 | s | — | $CH_3$ (a) | 1 |
| 3.1 | s | — | $CH_3$ (b) | 0.9 |
| 8.4 | s | — | $[P(C_2F_5)_3F_2(OCHNMe_2)]$ | 0.3 |

$^{13}$C-NMR spectroscopic data of $[P(C_2F_5)_3F_2(dmf)]$ in DMF

| δ, ppm | Multiplicity | J[Hz] | Assignment |
|---|---|---|---|
| 34.6 [a] | (hidden) | — | $CH_3$ (a) |
| 39.8 [a] | quar | $^1J(CH) = 143$ | $CH_3$ (b) |
| 117.0 [b] | d, m | $^1J(CP) = 249$ | —$CF_2CF_3$ |
| 119.0 [b] | d, m | $^2J(CP) = 30$ | —$CF_2CF_3$ |
| 163.2 [a] | d | $^1J(CH) = 218$ | $[P(C_2F_5)_3F_2(OCHNMe_2)]$ |

[a] $\{^1H\}$ [b] $\{^{19}F\}$

Example 13

Reaction of $[P(C_2F_5)_3F_2(dmf)]$ with $H_2O$

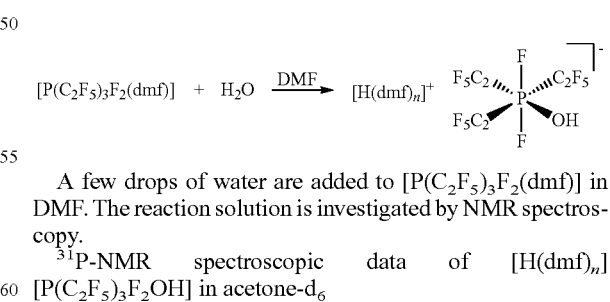

A few drops of water are added to $[P(C_2F_5)_3F_2(dmf)]$ in DMF. The reaction solution is investigated by NMR spectroscopy.

$^{31}$P-NMR spectroscopic data of $[H(dmf)_n]$ $[P(C_2F_5)_3F_2OH]$ in acetone-$d_6$

| δ, ppm | Multiplicity | J[Hz] | Assignment |
|---|---|---|---|
| −147.9 | t, sept | $^1J(PF) = 847$ $^2J(PF) = 86$ | $[H(dmf)_n][P(C_2F_5)_3F_2OH]$ |

$^{19}$F-NMR spectroscopic data of [H(dmf)$_n$][P(C$_2$F$_5$)$_3$F$_2$OH] in acetone-d$_6$

| δ, ppm | Multiplicity | J[Hz] | Assignment | Integral |
|---|---|---|---|---|
| −80.5 | m | — | trans-CF$_3$ | 1 |
| −81.5 | m | — | cis-CF$_3$ | 1.9 |
| −87.0 | d, m | $^1$J(PF) = 839 | PF | 0.6 |
| −114.5 | d | $^2$J(PF) = 85 | cis-, trans-CF$_2$ | 1.9 |

$^1$H-NMR spectroscopic data of [H(dmf)$_n$][P(C$_2$F$_5$)$_3$F$_2$OH] in acetone-d$_6$

| δ, ppm | Multiplicity | J[Hz] | Assignment | Integral |
|---|---|---|---|---|
| 2.7 | s | — | CH$_3$ (a) | 1.1 |
| 3.0 | s | — | CH$_3$ (b) | 1 |
| 8.8 | s | — | [H(OHCNMe$_2$)$_n$] | — |

Example 14

Reaction of [P(C$_2$F$_5$)$_3$F$_2$(dmf)] with EtOH

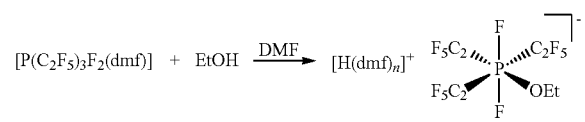

A few drops of ethanol are added to [P(C$_2$F$_5$)$_3$F$_2$(dmf)] in DMF. The reaction solution is investigated by NMR spectroscopy.

$^{31}$P-NMR spectroscopic data of [H(dmf)$_n$][P(C$_2$F$_5$)$_3$F$_2$OEt] in DMF

| δ, ppm | Multiplicity | J[Hz] | Assignment |
|---|---|---|---|
| −148.6 | t, pseudo-sept | $^1$J(PF) = 871 | [H(dmf)$_n$][P(C$_2$F$_5$)$_3$F$_2$OEt] |

$^{19}$F-NMR spectroscopic data of [H(dmf)$_n$][P(C$_2$F$_5$)$_3$F$_2$OEt] in DMF

| δ, ppm | Multiplicity | J[Hz] | Assignment | Integral |
|---|---|---|---|---|
| −79.2 | m | — | trans-CF$_3$ | 1 |
| −80.5 | m | — | cis-CF$_3$ | 1.9 |
| −93.1 | d, m | $^1$J(PF) = 871 | PF | 0.6 |
| −112.3 | d, m | $^2$J(PF) = 83 | trans-CF$_2$ | — |
| −113.1 | d, m | $^2$J(PF) = 86 | cis-CF$_2$ | — |

Example 15

Reaction of (C$_4$F$_9$)$_3$PF$_2$ with DMF

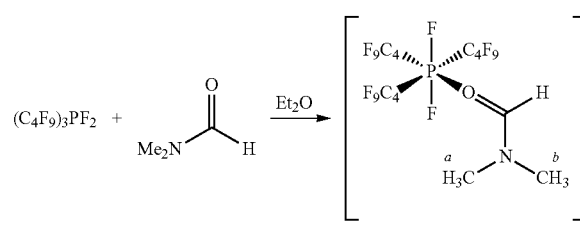

(C$_4$F$_9$)$_3$PF$_2$ is added to excess DMF. The reaction solution is investigated by NMR spectroscopy.

$^{31}$P-NMR spectroscopic data of [P(C$_4$F$_9$)$_3$F$_2$(dmf)] in DMF

| δ, ppm | Multiplicity | J[Hz] | Assignment |
|---|---|---|---|
| −135.5 | t, m | $^1$J(PF) = 999<br>$^2$J(PF) = 102 | [P(C$_4$F$_9$)$_3$F$_2$(dmf)] |

$^{19}$F-NMR spectroscopic data of [P(C$_4$F$_9$)$_3$F$_2$(dmf)] in DMF$^a$

| δ, ppm | Multiplicity | J[Hz] | Assignment | Integral |
|---|---|---|---|---|
| −82.1 | s | — | CF$_3$ | — |
| −108.1 | m | | CF$_2$ | — |
| −126.2 | | | | |

$^a$ The resonance of the fluorine atoms bonded to the phosphorus atom is covered by other resonances.

$^1$H-NMR spectroscopic data of [P(C$_4$F$_9$)$_3$F$_2$(dmf)] in DMF

| δ, ppm | Multiplicity | J[Hz] | Assignment | Integral |
|---|---|---|---|---|
| 2.7 | s | — | CH$_3$ (a) | 0.9 |
| 3.1 | s | — | CH$_3$ (b) | 1 |
| 8.4 | s | — | [P(C$_2$F$_9$)$_3$F$_2$(OCHNMe$_2$)] | 0.3 |

Example 16

Reaction of [P(C$_4$F$_9$)$_3$F$_2$(dmf)] with EtOH

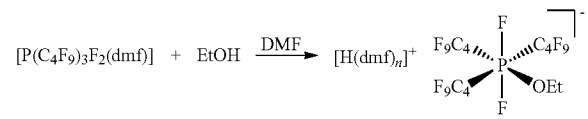

A few drops of ethanol are added to [P(C$_4$F$_9$)$_3$F$_2$(dmf)] in DMF. The reaction mixture is investigated by NMR spectroscopy.

$^{31}$P-NMR spectroscopic data of [H(dmf)$_n$][P(C$_4$F$_9$)$_3$F$_2$OEt] in DMF

| δ, ppm | Multiplicity | J[Hz] | Assignment |
|---|---|---|---|
| −143.3 | t, m | $^1$J(PF) = 903<br>$^2$J(PF) = 88 | [H(dmf)$_n$][P(C$_4$F$_9$)$_3$F$_2$OEt] |

$^{19}$F-NMR spectroscopic data of H[P(C$_4$F$_9$)$_3$F$_2$OEt]·nDMF in DMF

| δ, ppm | Multiplicity | J[Hz] | Assignment | Integral |
|---|---|---|---|---|
| −82.3 | m | — | CF$_3$ | — |
| −92.3 | d, m | $^1$J(PF) = 899 | PF | — |
| −109.6 | m | — | CF$_2$ | — |
| −127.6 | | | | |

Example 17

Preparation of [P(C$_2$F$_5$)$_2$F$_3$(dmf)]

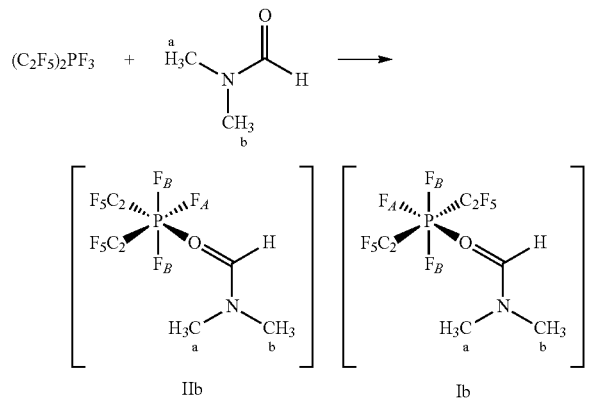

0.09 g (1.2 mmol) of DMF are initially introduced in about 15 ml of diethyl ether, and 1.5 mmol of (C$_2$F$_5$)$_2$PF$_3$ are condensed on. The reaction mixture is investigated by NMR spectroscopy. Two conformers, IIb and Ib, form on slow thawing. IIb is converted into Ib within a few hours at room temperature. After stirring at room temperature for 30 minutes, the solvent is removed in vacuo, leaving a colourless solid. Yield (based on DMF): 0.47 g (97%).

$^{31}$P-NMR spectroscopic data of the two conformers of [P(C$_2$F$_5$)$_2$F$_3$(dmf)] in DMF

| δ, ppm | Multiplicity | J[Hz] | Assignment |
|---|---|---|---|
| −146.6 | d, t, quin, d | $^1$J(PF$_A$) = 847<br>$^1$J(PF$_B$) = 922<br>$^2$J(PF) = 95<br>$^3$J(PH) = 7 | [P(C$_2$F$_5$)$_2$F$_3$(dmf)] (IIb) |
| −148.7 | d, t, quin | $^1$J(PF$_A$) = 947<br>$^1$J(PF$_B$) = 986<br>$^2$J(PF) = 108 | [P(C$_2$F$_5$)$_2$F$_3$(dmf)] (Ib) |

$^{19}$F-NMR spectroscopic data of the two conformers of [P(C$_2$F$_5$)$_2$F$_3$(dmf)] in DMF

| δ, ppm | Multiplicity | J[Hz] | Assignment | Integral |
|---|---|---|---|---|
| −58.7 | d, m | $^1$J(PF$_A$) = 848 | PF$_A$ (IIb) | 0.3 |
| −69.1 | d, m | $^1$J(PF$_A$) = 948 | PF$_A$ (Ib) | 0.8 |
| −74.9 | d, d, m | $^1$J(PF$_B$) = 987<br>$^2$J(F$_B$F$_A$) = 45 | PF$_B$ (Ib) | 1.7 |
| −76.2 | d, d, m | $^1$J(PF$_B$) = 922<br>$^2$J(F$_B$F$_A$) = 46 | PF$_B$ (IIb) | 0.7 |
| −82.7 | m | — | CF$_3$ (IIb) | 1.0 |
| −83.4 | m | — | CF$_3$ (IIb)/CF$_3$ (Ib) | 6.2 |
| −117.5 | d, m | $^2$J(PF) = 95 | CF$_2$ (IIb) | 0.6 |
| −118.7 | d, d, t, m | $^2$J(PF) = 108<br>$^3$J(FF$_A$) = 10<br>$^3$J(FF$_B$) = 11 | CF$_2$ (Ib) | 3.4 |
| −119.5 | d, m | $^2$J(PF) = 93 | CF$_2$ (IIb) | 0.6 |

$^1$H-NMR spectroscopic data of the two conformers of [P(C$_2$F$_5$)$_2$F$_3$(dmf)] in DMF

| δ, ppm | Multiplicity | J[Hz] | Assignment | Integral |
|---|---|---|---|---|
| 2.1 | s | — | CH$_3$ (a) (IIb) | 0.3 |
| 2.1 | s | — | CH$_3$ (a) (Ib) | 1 |
| 2.4 | s | — | CH$_3$ (b) (IIb) | 0.2 |
| 2.5 | s | — | CH$_3$ (b) (Ib) | 1 |
| 7.8 | s | — | [P(C$_2$F$_5$)$_2$F$_3$(OCHNMe$_2$)] (Ib) | 0.3 |
| 10.5 | s (br) | — | [P(C$_2$F$_5$)$_2$F$_3$(OCHNMe$_2$)] (IIb) | — |

$^{13}$C-NMR spectroscopic data of the two conformers of [P(C$_2$F$_5$)$_2$F$_3$(dmf)] in DMF

| δ, ppm | Multiplicity | J[Hz] | Assignment |
|---|---|---|---|
| 35.0 $^a$ | (hidden) | — | CH$_3$ (a) (Ib) |
| 40.0 $^a$ | quar | $^1$J(CH) = 144 | CH$_3$ (b) (Ib) |
| 115.5 $^b$ | d, m | $^1$J(CP) = 329 | −CF$_2$CF$_3$ |
| 119.4 $^b$ | d, m | $^2$J(CP) = 32 | −CF$_2$CF$_3$ |
| 163.4 $^a$ | d, t | $^1$J(CH) = 214 | [P(C$_2$F$_5$)$_2$F$_3$(OCHNMe$_2$)] (Ib) |

$^a$ {$^1$H}
$^b$ {$^{19}$F}

Example 18

Reaction of [P(C$_2$F$_5$)$_2$F$_3$(dmf)] with H$_2$O

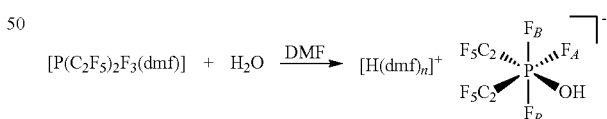

Water is condensed onto a solution of [P(C$_2$F$_5$)$_2$F$_3$(dmf)] (Ib) in DMF at −196° C. The reaction mixture is warmed to room temperature and investigated by NMR spectroscopy.

$^{31}$P-NMR spectroscopic data of [H(dmf)$_n$][P(C$_2$F$_5$)$_2$F$_3$OH] in DMF

| δ, ppm | Multiplicity | J[Hz] | Assignment |
|---|---|---|---|
| −154.4 | d, t, quin | $^1$J(PF$_A$) = 910<br>$^1$J(PF$_B$) = 926<br>$^2$J(PF) = 108 | [H(dmf)$_n$][P(C$_2$F$_5$)$_2$F$_3$OH] |

$^{19}$F-NMR spectroscopic data of [H(dmf)$_n$][P(C$_2$F$_5$)$_2$F$_3$OH] in DMF

| δ, ppm | Multiplicity | J[Hz] | Assignment | Integral |
|---|---|---|---|---|
| −63.2 | d, m | $^1$J(PF) = 910 | PF$_A$ | 0.6 |
| −76.0 | d, d, m | $^1$J(PF) = 926<br>$^2$J(FF) = 46 | PF$_B$ | 2 |
| −83.4 | d, t | $^3$J(PF) = 11<br>$^3$J(FF) = 7 | CF$_3$ | 6 |
| −118.9 | d, quar | $^2$J(PF) = 103<br>$^3$J(FF) = 10 | CF$_2$ | 4 |

Example 19

Reaction of [P(C$_2$F$_5$)$_2$F$_3$(dmf)] with EtOH

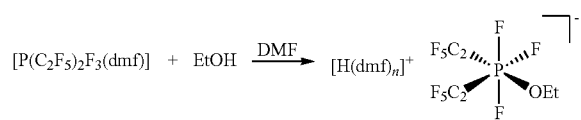

Ethanol is condensed onto a solution of [P(C$_2$F$_5$)$_2$F$_3$(dmf)] (Ib) in DMF at −196° C. The reaction mixture is warmed to room temperature and investigated by NMR spectroscopy.

$^{31}$P-NMR spectroscopic data of [H(dmf)$_n$][P(C$_2$F$_5$)$_2$F$_3$OEt] in DMF

| δ, ppm | Multiplicity | J[Hz] | Assignment |
|---|---|---|---|
| −152.6 | d, t, quin | $^1$J(PF$_A$) = 860<br>$^1$J(PF$_B$) = 876<br>$^2$J(PF) = 94 | [H(dmf)$_n$][P(C$_2$F$_5$)$_2$F$_3$OEt] |

$^{19}$F-NMR spectroscopic data of [H(dmf)$_n$][P(C$_2$F$_5$)$_2$F$_3$OEt] in DMF

| δ, ppm | Multiplicity | J[Hz] | Assignment | Integral |
|---|---|---|---|---|
| −57.2 | d, m | $^1$J(PF) = 860 | PF$_A$ | 1 |
| −78.5 | d, d, m | $^1$J(PF) = 876<br>$^2$J(FF) = 47 | PF$_B$ | 2.5 |
| −83.5 | d, t | $^3$J(PF) = 13<br>$^3$J(FF) = 7 | CF$_3$ | 8 |
| −119.3 | d, d, t | $^2$J(PF) = 94<br>$^3$J(FF$_A$) = 16<br>$^3$J(FF$_B$) = 8 | CF$_2$ | 5 |

Example 20

Reaction of (C$_2$F$_5$)$_3$PF$_2$— DMAP with 2-[2-(aminoethyl)-amino]ethanol

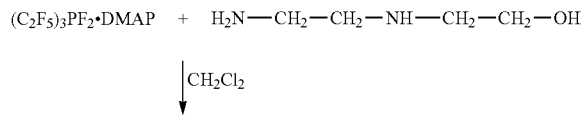

Experimental Procedure 6.50 g (11.86 mmol) of (C$_2$F$_5$)$_3$PF$_2$— DMAP in 80 ml of dichloromethane are initially introduced in a 100 ml Schlenk flask under protective gas, and 1.23 g (11.86 mmol) of 2-[2-(aminoethyl)amino]ethanol are added dropwise to the solution at 0° C. After the addition, the ice bath is removed, and the mixture is stirred at RT overnight. $^{19}$F- and $^{31}$P-NMR reaction checks are recorded next morning.

The reaction solution is then freed from CH$_2$Cl$_2$ and all volatile constituents in vacuo, leaving a slightly yellow powder.

Crude yield: 7.71 g (91.7% of theory)

If the reaction is carried out in DMF instead of in CH$_2$Cl$_2$, another isomer forms in which the two F atoms on the phosphorus are different.

NMR data: in CD$_2$Cl$_2$

| Nucleus | δ (ppm) | Splitting | Coupling | Assignment |
|---|---|---|---|---|
| $^{31}$P | −148.9 | t, sept | $^1$J$_{PF}$ = 879<br>$^2$J$_{PF}$ = 87 | —PF$_2$(C$_2$F$_5$)$_3$ |
| $^{19}$F | −94.6 | d | $^1$J$_{PF}$ = 879 | —PF$_2$(CF$_2$CF$_3$)$_3$ |
|  | −81.2 | m |  | —PF$_2$(CF$_2$CF$_3$)$_3$ (6F) |
|  | −80.0 | m |  | —PF$_2$(CF$_2$CF$_3$)$_3$ (3F) |
|  | −113.4 | m |  | —PF$_2$(CF$_2$CF$_3$)$_3$ (4F) |
|  | −113.7 | m |  | —PF$_2$(CF$_2$CF$_3$)$_3$ (2F) |
| $^1$H | 8.02 | d | $^3$J$_{HH}$ = 7.0 | DMAP (2H) |
|  | 6.67 | d | $^3$J$_{HH}$ = 7.0 | DMAP (2H) |
|  | 5.61 | s, br |  | 4H |
|  | 4.19 | m |  | 2H |
|  | 3.13 | s |  | DMAP (6H) |
|  | 2.89 | m |  | 6H |
| $^{13}$C | 155.9 | s |  | DMAP |
|  | 144.1 | s |  | DMAP |
|  | 106.8 | s |  | DMAP |
|  | 63.2 | m |  | —O—CH$_2$— |
|  | 48.9 | d | $^3$J$_{CP}$ = 8.7 | —O—CH$_2$—CH$_2$—N— |
|  | 48.1 | s |  | H$_2$N—(CH$_2$)$_2$—N— |
|  | 39.2 | s |  | DMAP |
|  | 38.2 | s |  | H$_2$N—(CH$_2$)$_2$—N— |

Example 21

Reaction of (C$_2$F$_5$)$_3$PF$_2$·DMAP with ethyl 6-hydroxyhexanoate

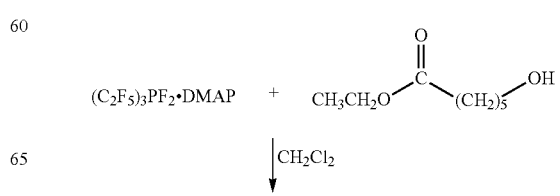

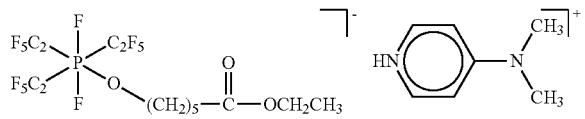
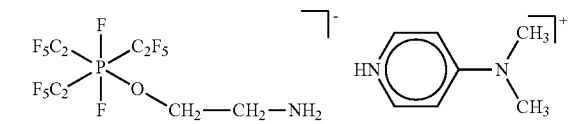

Experimental Procedure 3.30 g (6.02 mmol) of (C$_2$F$_5$)$_3$PF$_2$·DMAP in 40 ml of dichloromethane are initially introduced in a 100 ml Schlenk flask under protective gas, and 0.96 g (6.02 mmol) of ethyl 6-hydroxyhexanoate is added dropwise to the solution at 0° C. After the addition, the ice bath is removed, and the mixture is stirred at RT overnight. $^{19}$F- and $^{31}$P-NMR reaction checks are recorded next morning.

The reaction solution is freed from CH$_2$Cl$_2$ and all volatile constituents in vacuo, leaving an orange oil.

Crude yield: 4.2 g (98.6% of theory

NMR data: in CD$_2$Cl$_2$

| Nucleus | δ (ppm) | Splitting | Coupling | Assignment |
|---|---|---|---|---|
| $^{31}$P | −147.9 | t, sept | $^1J_{PF}$ = 870  $^2J_{PF}$ = 89 | —PF$_2$(C$_2$F$_5$)$_3$ |
| $^{19}$F | −94.4 | d | $^1J_{PF}$ = 870 | —PF$_2$(CF$_2$CF$_3$)$_3$ |
|  | −80.9 | m |  | —PF$_2$(CF$_2$CF$_3$)$_3$ (6F) |
|  | 79.8 | m |  | —PF$_2$(CF$_2$CF$_3$)$_3$ (3F) |
|  | −113.0 | m |  | —PF$_2$(CF$_2$CF$_3$)$_3$ (4F) |
|  | −113.3 | m |  | —PF$_2$(CF$_2$CF$_3$)$_3$ (2F) |
| $^1$H | 7.92 | d | $^3J_{HH}$ = 7.0 | DMAP (2H) |
|  | 6.80 | d | $^3J_{HH}$ = 7.0 | DMAP (2H) |
|  | 4.13 | q |  | —O—CH$_2$CH$_3$ (2H) |
|  | 3.99 | q |  | —O—(CH$_2$)$_4$—CH$_2$— (2H) |
|  | 3.26 | s |  | DMAP (6H) |
|  | 2.32 | t | $^3J_{HH}$ = 7.4 | —O—(CH$_2$)$_4$—CH$_2$—C(O)— (2H) |
|  | 1.62 | m |  |  |
|  | 1.53 | m |  | —O—(CH$_2$)$_4$—CH$_2$— (2H) |
|  | 1.32 | m |  | —O—(CH$_2$)$_4$—CH$_2$— (2H) |
|  | 1.27 | t | $^3J_{HH}$ = 7.0 | —O—(CH$_2$)$_4$—CH$_2$— (2H) —O—CH$_2$—CH$_3$ (3H) |
| $^{13}$C | 174.8 | s |  | —C(O)— |
|  | 157.5 | s |  | DMAP |
|  | 138.4 | s |  | DMAP |
|  | 107.1 | s |  | DMAP |
|  | 66.8 | m |  | —O—CH$_2$—(CH$_2$)$_4$— |
|  | 60.5 | s |  | —O—CH$_2$CH$_3$ |
|  | 40.0 | s |  | DMAP |
|  | 34.3 | s |  | —O—CH$_2$—CH$_2$— |
|  | 30.7 | d | $^3J_{PC}$ = 8.1 | (CH$_2$)$_3$— |
|  | 25.2 | s |  | —O—CH$_2$—CH$_2$— (CH$_2$)$_3$— |
|  | 24.7 | s |  |  |
|  | 13.8 | s |  | —O—CH$_2$—CH$_2$— (CH$_2$)$_3$— —O—CH$_2$—CH$_3$ |

Example 22

(C$_2$F$_5$)$_3$PF$_2$·DMAP with Ethanolamine

4.27 g (7.79 mmol) of (C$_2$F$_5$)$_3$PF$_2$·DMAP in 60 ml of dichloromethane are initially introduced in a 100 ml Schlenk flask under protective gas, and 0.48 g (7.79 mmol) of ethanolamine is added dropwise to the solution at 0° C. After the addition, the ice bath is removed, and the mixture is stirred at RT overnight. $^{19}$F- and $^{31}$P-NMR reaction checks are recorded next morning. The reaction solution is then freed from CH$_2$Cl$_2$ and all volatile constituents in vacuo, leaving a slightly yellow powder.

Crude yield: 4.55 g (95.8% of theory)

NMR data: in CD$_2$Cl$_2$

| Nucleus | δ (ppm) | Splitting | Coupling | Assignment |
|---|---|---|---|---|
| $^{31}$P | −148.4 | t, sept | $^1J_{PF}$ = 875  $^2J_{PF}$ = 87 | —PF$_2$(C$_2$F$_5$)$_3$ |
| $^{19}$F | −94.7 | d | $^1J_{PF}$ = 875 | —PF$_2$(CF$_2$CF$_3$)$_3$ |
|  | −81.3 | m |  | —PF$_2$(CF$_2$CF$_3$)$_3$ (6F) |
|  | −80.0 | m |  | —PF$_2$(CF$_2$CF$_3$)$_3$ (3F) |
|  | −113.3 | m |  | —PF$_2$(CF$_2$CF$_3$)$_3$ (4F) |
|  | −113.5 | m |  | —PF$_2$(CF$_2$CF$_3$)$_3$ (2F) |
| $^1$H | 8.00 | d | $^3J_{HH}$ = 5.2 | DMAP (2H) |
|  | 7.73 | s, br |  | —NH$_2$ (2H) |
|  | 6.73 | d | $^3J_{HH}$ = 5.2 | DMAP (2H) |
|  | 4.15 | m |  | —O—(CH$_2$)— |
|  | 3.19 | s |  | NH$_2$(2H) |
|  | 2.94 | m |  | DMAP (6H) |
|  | 156.7 | s |  | —O—(CH$_2$)— |
|  | 141.4 | s |  | NH$_2$(2H) |
| $^{13}$C | 106.9 | s |  | DMAP |
|  | 65.2 | m |  | DMAP |
|  | 41.8 | d |  | DMAP |
|  | 39.6 | s | $^3J_{CP}$ = 8.7 | —O—CH$_2$—CH$_2$—NH$_2$ —O—CH$_2$—CH$_2$—NH$_2$ DMAP |

Note:
If the reaction is carried out in DMF instead of in CH$_2$Cl$_2$, another isomer forms in which the two F atoms on the phosphorus are different.

Example 23

Reaction of (C$_2$F$_5$)$_3$PF$_2$·DMAP with 2-methoxyethanol (C$_2$F$_5$)$_3$PF$_2$·DMAP    +    HO—CH$_2$—CH$_2$—O—CH$_3$ ↓ CH$_2$Cl$_2$ 3.86 g (7.04 mmol) of (C$_2$F$_5$)$_3$PF$_2$— DMAP in 60 ml of dichloromethane are initially introduced in a 100 ml Schlenk flask under protective gas, and 0.54 g (7.04 mmol) of 2-methoxyethanol is added dropwise to the solution at 0° C. After the addition, the ice bath is removed, and the mixture is stirred at RT overnight. $^{19}$F- and $^{31}$P-NMR reaction checks are recorded next morning.

The reaction solution is then freed from $CH_2Cl_2$ and all volatile constituents in vacuo, leaving a slightly yellow powder.

Crude yield: 4.38 g (99.8% of theory)

NMR data: in $CD_2Cl_2$

| Nucleus | δ (ppm) | Splitting | Coupling | Assignment |
|---|---|---|---|---|
| $^{31}$P | −147.8 | t, sept | $^1J_{PF}$ = 878<br>$^2J_{PF}$ = 89 | —$PF_2(C_2F_5)_3$ |
| $^{19}$F | −94.8 | d | $^1J_{PF}$ = 878 | —$PF_2(CF_2CF_3)_3$ |
|  | −81.0 | m |  | —$PF_2(CF_2CF_3)_3$ (6F) |
|  | −79.9 | m |  | —$PF_2(CF_2CF_3)_3$ (3F) |
|  | −113.2 | m |  | —$PF_2(CF_2CF_3)_3$ (4F) |
|  | −113.5 | m |  | —$PF_2(CF_2CF_3)_3$ (2F) |
| $^1$H | 8.03 | d | $^3J_{HH}$ = 6.3 | DMAP (2H) |
|  | 6.75 | d | $^3J_{HH}$ = 6.3 | DMAP (2H) |
|  | 4.27 | m |  | —O—$(CH_2)_2$—O— |
|  | 3.62 | m |  | $CH_3$(2H) |
|  | 3.32 | s |  | —O—$(CH_2)_2$—O— |
|  | 3.24 | s |  | $CH_3$(2H) |
|  | 157.3 | s |  | —O—$CH_3$ |
|  | 139.3 | s |  | DMAP (6H) |
| $^{13}$C | 106.6 | s |  | DMAP |
|  | 73.5 | d | $^3J_{CP}$ = 7.9 | DMAP |
|  | 65.6 | m |  | DMAP |
|  | 57.6 | s |  | —O—$CH_2$—$CH_2$—O—$CH_3$ |
|  | 40.1 | s |  | —O—$CH_2$—$CH_2$—O—$CH_3$ |
|  |  |  |  | —O—$CH_3$ |
|  |  |  |  | DMAP |

Example 24

$Mg[(C_2F_5)_3PF_2(OH)]_2$ 4.48 g (10.5 mmol) of tris(pentafluoroethyl)difluorophosphorane are dissolved in 20 ml of $Et_2O$ and cooled to −60° C. A suspension of 0.24 g (6.0 mmol) of magnesium oxide in 18 ml of water is subsequently added in one portion, the mixture is warmed to 0° C., the $Et_2O$ phase is separated off and washed with 20 ml of ice-water. According to $^{19}$F-NMR investigations, the $Et_2O$ solution is composed of: 81% of $Mg[(C_2F_5)_3PF_2(OH)]_2$, 12% of magnesium tris(pentafluoroethyl)trifluorophosphate (FAP) and 7% of magnesium bis(pentafluoroethyl)phosphinate.

The collected aqueous phase is extracted with 10 ml of $Et_2O$, and the combined $Et_2O$ solution is evaporated to dryness in vacuo, giving 3.64 g of a pale-pink solid.

Example 25

$Na[(C_2F_5)_3PF_2(OH)]$ 4.26 g (10.0 mmol) of tris(pentafluoroethyl)difluorophosphorane are dissolved in 20 ml of $Et_2O$ and cooled to −60° C., 20.5 ml of an aqueous 0.5 M sodium hydroxide solution are subsequently added dropwise. The mixture is warmed to 0° C., the $Et_2O$ phase is separated off and washed with 20 ml of ice-water. The collected aqueous phase is extracted with 10 ml of $Et_2O$, and the combined $Et_2O$ solution is evaporated to dryness in vacuo, giving 1.96 g of a white solid.

According to $^{19}$F-NMR spectroscopic investigations of the reaction solution, the $Et_2O$ phase consists virtually exclusively (>95%) of $Na[(C_2F_5)_3PF_2(OH)]$. After work-up and evaporation of the separated-off ethereal phase to dryness, the solid obtained is, according to $^{19}$F-NMR, composed of 55% of $Na[(C_2F_5)_3PF_2(OH)]$, 30% of sodium tris(pentafluoroethyl)trifluorophosphate (FAP) and 15% of sodium bis(pentafluoroethyl)phosphinate.

NMR data (solvent: $CD_3CN$; reference substance: $^1$H, TMS; $^{19}$F, $CCl_3F$; $^{31}$P, 85% $H_3PO_4$):

Sodium tris(pentafluoroethyl)difluorohydroxyphosphate:
$^1$H, δ, ppm=4.83 t (1H), $^3J_{H,F}$=14 Hz;
$^{19}$F, δ, ppm=−81.3 s (3F, $CF_3$); −82.3 s (6F, 2$CF_3$); −87.5 d, m (2F, $PF_2$),
$^1J_{P,F}$=842 Hz; −114.8 d, m (6F, 3$CF_2$), $^2J_{P,F}$=86 Hz;
$^{31}$P, δ, ppm=−147.3 t, sept; $^1J_{P,F}$=842 Hz, $^2J_{P,F}$=86 Hz.

Example 26

$K[(C_2F_5)_3PF_2(OH)]$ 4.58 g (10.8 mmol) of tris(pentafluoroethyl)difluorophosphorane are dissolved in 20 ml of $Et_2O$ and cooled to −60° C. 22 ml of an aqueous 0.5 M potassium hydroxide solution are subsequently added dropwise. The mixture is warmed to 0° C., the $Et_2O$ phase is separated off and washed with 20 ml of ice-water. The collected aqueous phase is extracted with 10 ml of $Et_2O$, and the combined $Et_2O$ solution is evaporated to dryness in vacuo, giving 3.59 g of a white solid. The solid obtained is, according to $^{19}$F-NMR, composed of 87% of $K[(C_2F_5)_3PF_2(OH)]$, 10% of potassium tris(pentafluoroethyl)trifluorophosphate (FAP) and 3% of potassium bis(pentafluoroethyl)-phosphinate.

NMR data (solvent: $CD_3CN$; reference substance: $^1$H, TMS; $^{19}$F, $CCl_3F$; $^{31}$P, 85% $H_3PO_4$):

Potassium tris(pentafluoroethyl)difluorohydroxyphosphate:
$^1$H, δ, ppm=3.27 br.s (1H);
$^{19}$F, δ, ppm=−80.7 m (3F, $CF_3$); −81.7 m (6F, $CF_3$); −87.0 d, m (2F, $PF_2$),
$^1J_{P,F}$=842 Hz; −114.6 d, m (6F, 3$CF_2$), $^2J_{P,F}$=85 Hz;
$^{31}$P, δ, ppm=−147.2 t, sept, $^1J_{P,F}$=842 Hz, $^2J_{P,F}$=85 Hz.

Example 27

$Cs[(C_2F_5)_3PF_2(OH)]$ 4.30 g (10.1 mmol) of tris(pentafluoroethyl)difluorophosphorane are dissolved in 20 ml of $Et_2O$ and cooled to −60° C. 26 ml of an aqueous 0.5 M caesium hydroxide solution are subsequently added dropwise. The mixture is warmed to 0° C., the $Et_2O$ phase is separated off and washed with 20 ml of ice-water. The collected aqueous phase is extracted with 10 ml of $Et_2O$, and the combined $Et_2O$ solution is evaporated to dryness in vacuo, giving 4.18 g of a white solid. The solid obtained is, according to $^{19}$F-NMR, composed of 94% of $Cs[(C_2F_5)_3PF_2(OH)]$, 5% of caesium tris(pentafluoroethyl)-trifluorophosphate (FAP) and 1% of caesium bis(pentafluoroethyl)phosphinate.

NMR data (solvent: $CD_3CN$; reference substance: $^1$H, TMS; $^{19}$F, $CCl_3F$; $^{31}$P, 85% $H_3PO_4$):

Caesium tris(pentafluoroethyl)difluorohydroxyphosphate:
$^1$H, δ, ppm=4.83 t (1H), $^3J_{H,F}$=14 Hz;
$^{19}$F, δ, ppm=−80.7 s (3F, $CF_3$); −81.7 s (6F, 2$CF_3$); −87.0 d, m (2F, $PF_2$),
$^1J_{P,F}$=842 Hz; −114.6 d, m (6F, 3$CF_2$), $^2J_{P,F}$=85 Hz;
$^{31}$P, δ, ppm=−147.2 t, sept, $^1J_{P,F}$=842 Hz, $^2J_{P,F}$=85 Hz.

Example 28

$[(CH_3)_4N]^+[(C_2F_5)_3PF_2OH]^−$ 3.63 g (8.5 mmol) of tris(pentafluoroethyl)difluorophosphorane are cooled to −50° C., and 3.13 g (8.6 mmol) of an aqueous 25% solution of tetramethyl-ammonium hydroxide are added. The white precipitate was filtered off and dried in vacuo, giving 3.4 g of a white solid. The solid obtained is, according to $^{19}$F-NMR, composed of 74% of hydroxyl complex $[(CH_3)_4N]^+[(C_2F_5)_3\text{—}PF_2OH]^-$, 4% of tetramethylammonium tris(pentafluoroethyl)trifluorophosphate (FAP) and 22% of tetramethylammonium bis(pentafluoroethyl)phosphinate.

NMR data (solvent: $CD_3CN$; reference substance: $^1$H, TMS; $^{19}$F, $CCl_3F$; $^{31}$P, 85% $H_3PO_4$): Tris(pentafluoroethyl) difluorohydroxyphosphate tetramethylammonium salt, hydroxyl complex:

$^1$H, δ, ppm=3.07 s, (12H, 4CH$_3$); 4.92 t,d (1H), $^3J_{H,F}$=14 Hz, $^2J_{P,H}$=2 Hz.

$^{19}$F, δ, ppm=−80.7 m (3F, CF$_3$); −81.8 m (6F, 2CF$_3$); −87.3 d, m (2F, PF$_2$), $^1J_{P,F}$=842 Hz; −114.7 d, m (6F, 3CF$_2$), $^2J_{P,F}$=86 Hz.

$^{31}$P, δ, ppm=−147.2 t, sept, $^1J_{P,F}$=842 Hz, $^2J_{P,F}$=86 Hz.

Example 29

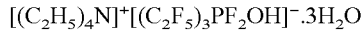

4.46 g (10.5 mmol) of tris(pentafluoroethyl)difluorophosphorane are dissolved in 20 ml of Et$_2$O and cooled to −60° C. 17.2 g (10.7 mmol) of an aqueous tetraethylammonium hydroxide solution (about 0.6 M) are subsequently added dropwise. The mixture is warmed to 0° C., and the white solid which precipitates is filtered off and dried in air, giving 5.66 g of a white solid, which, according to $^{19}$F-NMR and $^1$H-NMR spectra, consists of 95% of $[(C_2H_5)_4N]^+$ $[(C_2F_5)_3PF_2OH]^-.3H_2O$. Yield is 86%. On drying of the solid overnight in vacuo, this complex eliminates water and C$_2$F5H and forms $[(C_2H_5)_4N]^+[(C_2F5)_2P\ F_2O]^-$.

NMR data (solvent: $CD_3CN$; reference substance: $^1$H, $^{13}$C, TMS; $^{19}$F, $CCl_3F$; $^{31}$P, 85% $H_3PO_4$):

Tris(pentafluoroethyl)difluorohydroxyphosphate tetraethylammonium salt.3H$_2$O, hydroxyl complex.3H$_2$O:

$^1$H, δ, ppm=1.20 t,t (12H, 4CH$_3$), $^3J_{H,H}$=7 Hz, $^3J_{H,14N}$=2 Hz; 2.22 s, (6H, 3H$_2$O); 3.14 q (8H, 4CH$_2$), $^3J_{H,H}$=7 Hz; 4.86 t,d (1H), $^3J_{H,F}$=14 Hz, $^2J_{H,P}$=2 Hz.

$^{13}$C{$^1$H}, δ, ppm=115-128 m, (CF$_2$CF$_3$); 53.2 t, (4C, CH$_2$), $^1J_{14N,13C}$=3 Hz; 7.7 s, (4C, CH$_3$).

$^{19}$F, δ, ppm=−80.7 m (3F, CF$_3$); −81.8 m (6F, 2CF$_3$); −87.4 d, m (2F, PF$_2$), $^1J_{P,F}$=842 Hz; −114.8 d, m (6F, 3CF$_2$), $^2J_{P,F}$=86 Hz.

$^{31}$P, δ, ppm=−147.3 t, sept, $^1J_{P,F}$=842 Hz, $^2J_{P,F}$=86 Hz.

Example 30

$[(C_4H_9)_4N]^+[(C_2F_5)_3PF_2OCH_3]^-$ 4.20 g (9.9 mmol) of tris(pentafluoroethyl)difluorophosphorane are cooled to −50° C., and 10 ml (10 mmol) of a 1M solution of tetrabutylammonium hydroxide in methanol are added with vigorous stirring. According to $^{19}$F- and $^1$H-NMR spectra, a mixture consisting of two complexes:

$[(C_4H_9)_4N]^+[(C_2F_5)_3PF_2OH]^-$ and $[(C_4H_9)_4N]^+$ $[(C_2F_5)_3PF_2OCH_3]^-$, is formed. Removal of volatile constituents gives 6.0 g of white solid, which, according to $^{19}$F- and $^1$H-NMR spectra, consists of 40% of $[(C_4H_9)_4N]^+$ $[(C_2F_5)_2PF_2O]^-$ and 60% of $[(C_4H_9)_4N+$ $[(C_2F_5)_3PF_2OCH_3]^-$.

NMR data (solvent: methanol; lock: $CD_3CN$; reference substance: $^1$H, TMS; $^{19}$F, $CCl_3F$; $^{31}$P, 85% $H_3PO_4$):

Tris(pentafluoroethyl)difluorohydroxyphosphate tetrabutylammonium salt, hydroxyl complex:

$^1$H, δ, ppm=0.98 t (12H, 4CH$_3$), $^3J_{H,H}$=7 Hz; 1.36 m, (8H, 4CH$_2$); 1.61 m, (8H, 4CH$_2$); 3.10 m, (8H, 4CH$_2$); 4.86 t,d (1H), $^3J_{H,F}$=14 Hz, $^2J_{H,P}$=2 Hz.

$^{19}$F, δ, ppm=−80.7 m (3F, CF$_3$); −81.8 m (6F, 2CF$_3$); −87.4 d, m (2F, PF$_2$), $^1J_{P,F}$=842 Hz; −114.8 d, m (6F, 3CF$_2$), $^2J_{P,F}$=86 Hz.

$^{31}$P, δ, ppm=−147.3 t, sept, $^1J_{P,F}$=842 Hz, $^2J_{P,F}$=86 Hz.

Tris(pentafluoroethyl)difluoromethoxyphosphate tetrabutylammonium salt, $[(C_4H_9)_4N]^+[(C_2F5)_3P\ F_2OCH_3]^-$.

$^1$H, δ, ppm=0.98 t (12H, 4CH$_3$), $^3J_{H,H}$=7 Hz; 1.36 m, (8H, 4CH$_2$); 1.61 m, (8H, 4CH$_2$); 3.10 m, (8H, 4CH$_2$); 3.56 d, m (3H, CH$_3$), $^3J_{H,P}$=13 Hz.

$^{19}$F, δ, ppm=−80.7 m (3F, CF$_3$); −81.8 m (6F, 2CF$_3$); −95.9 d, m (2F, PF$_2$), $^1J_{P,F}$=867 Hz; −114.1 d, m (6F, 3CF$_2$), $^2J_{P,F}$=84 Hz.

$^{31}$P, δ, ppm=−148.5 t, sept, q, $^1J_{P,F}$=867 Hz, $^2J_{P,F}$=84 Hz, $^3J_{P,H}$=13 Hz.

Bis(pentafluoroethyl)difluorooxophosphorane tetrabutylammonium salt, $[(C_2F_5)_2PF_2O]^-[(C_4H_9)_4N]^+$:

$^1$H, δ, ppm=0.98 t (12H, 4CH$_3$), $^3J_{H,H}$=7 Hz; 1.36 m, (8H, 4CH$_2$); 1.61 m, (8H, 4CH$_2$); 3.10 m, (8H, 4CH$_2$); 3.56 d, m (3H, CH$_3$), $^3J_{H,P}$=13 Hz.

$^{19}$F, δ, ppm=−67.5 d, m (2F, PF$_2$), $^1J_{P,F}$=1108 Hz; −81.9 t, (6F, 2CF$_3$), $^4J_{F,F}$=11 Hz; −124.8 d, t (4F, 2CF$_2$), $^2J_{P,F}$=78 Hz; $^3J_{F,F}$=7 Hz.

$^{31}$P, δ, ppm=−62.5 t, quin, $^1J_{P,F}$=1108 Hz, $^2J_{P,F}$=78 Hz.

Example 31

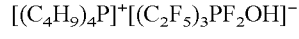

4.66 g (10.9 mmol) of tris(pentafluoroethyl)difluorophosphorane are dissolved in 20 ml of Et$_2$O and cooled to −60° C. 20 ml (10.9 mmol) of an aqueous tetrabutylphosphonium hydroxide 0.55M solution are subsequently added with vigorous stirring. The mixture is warmed to 0° C., and the white solid which precipitates is filtered off and dried in air, giving 5.68 g of a white solid, which, according to $^{19}$F NMR spectrum, consists of 85% of hydroxyl complex $[(C_4H_9)_4P]^+$ $[(C_2F_5)_3PF_2OH]^-$, 11% of tetrabutylphosphonium tris(pentafluoroethyl)trifluorophosphate (FAP) and 4% of tetrabutylphosphonium bis(pentafluoroethyl)phosphinate.

NMR data (solvent: $CD_3CN$; reference substance: $^{19}$F, $CCl_3F$; $^{31}$P, 85% $H_3PO_4$):

Tris(pentafluoroethyl)difluorohydroxyphosphate tetrabutylphosphonium salt, hydroxyl complex:

$^{19}$F, δ, ppm=−80.7 m (3F, CF$_3$); −81.7 m (6F, 2CF$_3$); −87.0 d, m (2F, PF$_2$), $^1J_{P,F}$=842 Hz; −114.6 d, m (6F, 3CF$_2$), $^2J_{P,F}$=85 Hz.

$^{31}$P, δ, ppm=−147.2 t, sept, $^1J_{P,F}$=842 Hz, $^2J_{P,F}$=85 Hz.

Example 32

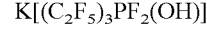

0.98 g (10 mmol) of potassium acetate are dissolved in 10 ml of water, and 4.34 g (10.2 mmol) of tris(pentafluoroethyl) difluorophosphorane are added slowly at 0° C. with vigorous stirring. After 10 minutes, all volatile components are removed at 0° C. in vacuo, giving 4.9 g of a colourless solid, which, according to $^{19}$F-NMR spectrum, consists of 91% of K[(C$_2$F$_5$)$_3$PF$_2$(OH)]hydroxyl complex, 6% of potassium tris (pentafluoroethyl)trifluorophosphate (FAP) and 3% of potassium bis(pentafluoroethyl)phosphinate. The substance exhibits a weight loss of 24% at 104° C., which corresponds to liberation of $C_2F_5H$.

Potassium tris(pentafluoroethyl)difluorohydroxyphosphate, hydroxyl complex:

NMR data (solvent: $CD_3CN$; reference substance: $^{19}F$, $CCl_3F$; $^{31}P$, 85% $H_3PO_4$):

$^{19}F$, δ, ppm=−80.7 m (3F, $CF_3$); −81.7 m (6F, $2CF_3$); −87.0 d, m (2F, $PF_2$), $^1J_{P,F}$=842 Hz; −114.6 d (6F, $3CF_2$), $^2J_{P,F}$=85 Hz.

$^{31}P$, δ, ppm=−147.2 t, sept, $^1J_{P,F}$=842 Hz, $2J_{P,F}$=85 Hz.

Example 33

Reaction with Potassium Acetate, $CH_3C(O)OK$, in Acetonitrile

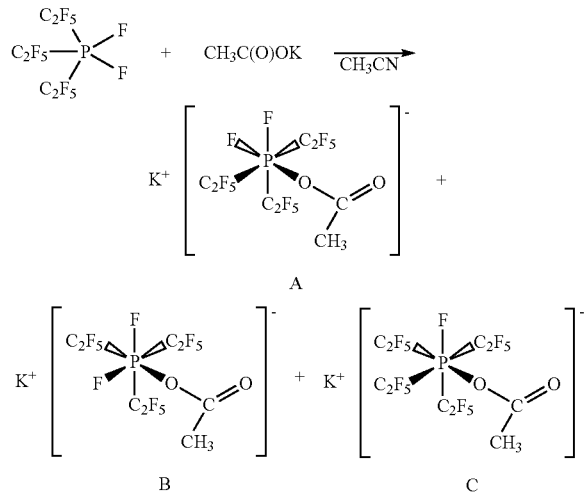

a) 0.66 g (6.7 mmol) of potassium acetate are initially introduced in 10 ml of acetonitrile, and 3.14 g (7.4 mmol) of tris(pentafluoroethyl)difluorophosphorane are added at 0° C. with vigorous stirring. The cooling bath is removed, and the reaction mixture is warmed to room temperature. After stirring for 15 minutes and dissolution of the potassium acetate, all volatile components are removed in vacuo, giving 3.37 g (yield: 96%) of a colourless solid, which, according to $^{19}F$-NMR spectrum, consists of a 1:1 mixture of complexes (A) and (B).

NMR data (solvent: $CD_3CN$; reference substance: $^1H$, TMS; $^{19}F$, $CCl_3F$; $^{31}P$, 85% $H_3PO_4$):

Complex A $^1H$, δ, ppm=2.02 d (3H, $CH_3C(O)$), $^4J_{H,P}$=1 Hz.

$^{19}F$, δ, ppm=−46.4 d, m (1F, $PF_2$), $^1J_{P,F}$=914 Hz; −79.7 d, m (1F, $PF_2$) $^1J_{P,F}$=862 Hz; −81.0 m (3F, $CF_3$); −82.6 m (6F, $2CF_3$); −113.6 d, d (4F, $2CF_2$), $^2J_{F(A),F(B)}$=292 Hz, $^2J_{P,F}$=104 Hz; −119.3 d, d (2F, $CF_2$), $^2J_{F(A),F(B)}$=292 Hz, $^2J_{P,F}$=90 Hz.

$^{31}P$, δ, ppm=−148.1 d, d,t,quin, $^1J_{P,F}$=914 Hz, $^1J_{P,F}$=862 Hz, $^2J_{P,F}$=104 Hz; $^2J_{P,F}$=90 Hz.

Complex B $^1H$, δ, ppm=1.94 d (3H, $CH_3C(O)$), $^4J_{H,P}$=2 Hz;

$^{19}F$, δ, ppm=−62.0 d, m (2F, $PF_2$) $^1J_{P,F}$=826 Hz; −82.7 m (6F, $2CF_3$); −83.1 m (3F, $CF_3$); −114.0 d, m (4F, $2CF_2$), $^2J_{P,F}$=78 Hz; −114.8 d, m (2F, $CF_2$), $2J_{P,F}$=78 Hz;

$^{31}P$, δ, ppm=−151.3 t, sept, $^1J_{P,F}$=826 Hz, $^2J_{P,F}$=78 Hz.

b) 0.25 g (2.5 mmol) of potassium acetate are initially introduced in 15 ml of acetonitrile, and 1.10 g (2.6 mmol) of tris(pentafluoroethyl)difluorophosphorane are added at 0° C., and the mixture is stirred vigorously for two hours. All volatile constituents are subsequently removed in vacuo over the course of two hours, giving 1.30 g (yield: 98%) of a colourless solid, which, according to $^{19}F$-NMR spectrum, consists of a 6:1 mixture of complexes (C) and (B).

NMR data (solvent: $CD_3CN$; reference substance: $^1H$, TMS; $^{19}F$, $CCl_3F$; $^{31}P$, 85% $H_3PO_4$):

Complex C $^1H$, δ, ppm=1.97 s ($CH_3$).

$^{19}F$, δ, ppm=−81.4 m (3F, $CF_3$); −82.5 m (6F, $2CF_3$); −88.9 d, m (2F, $PF_2$) $^1J_{P,F}$=912 Hz; −115.7 d, m (4F, $2CF_2$), $^2J_{P,F}$=85 Hz; −116.6 d, m (2F, $CF_2$), $^2J_{P,F}$=103 Hz;

$^{31}P$, δ, ppm=−144.1 t,quin,t, $^1J_{P,F}$=912 Hz, $^2J_{P,F}$=103 Hz; $^2J_{P,F}$=85 Hz.

Complex B $^1H$, δ, ppm=1.94 d (3H, $CH_3C(O)$), $^4J_{H,P}$=2 Hz;

$^{19}F$, δ, ppm=−62.0 d, m (2F, $PF_2$) $^1J_{P,F}$=826 Hz; −82.7 m (6F, $2CF_3$); −83.1 m (3F, $CF_3$); −114.0 d, m (4F, $2CF_2$), $^2J_{P,F}$=78 Hz; −114.8 d, m (2F, $CF_2$), $2J_{P,F}$=78 Hz;

$^{31}P$, δ, ppm=−151.3 t, sept, $^1J_{P,F}$=826 Hz, $^2J_{P,F}$=78 Hz.

c) 0.44 g (4.5 mmol) of potassium acetate are initially introduced in 10 ml of acetonitrile, and 1.90 g (4.5 mmol) of tris(pentafluoroethyl)difluorophosphorane are added at 0° C., and the mixture is stirred vigorously for one hours. All volatile constituents are subsequently removed overnight in vacuo, giving 2.30 g (yield: 98%) of a colourless solid, which, according to $^{19}F$-NMR spectrum, consists of a 3:16:1 mixture of complexes (A), (B) and (C).

Example 34

Reaction with tetrabutylammonium acetate, $[(C_4H_9)_4N]^+$ $[CH_3C(O)O]^-$ in acetonitrile

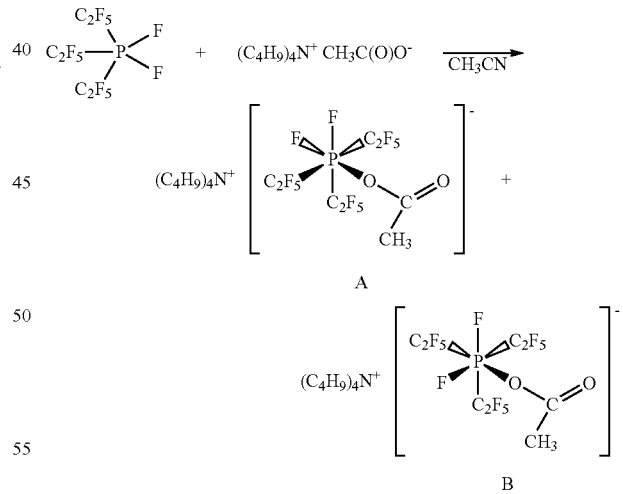

2.11 g (7 mmol) of tetrabutylammonium acetate (dried in an oil-pump vacuum at 100° C. for one hour) are dissolved in 20 ml of acetonitrile, and 3.11 g (7.3 mmol) of tris(pentafluoroethyl)difluorophosphorane are added at room temperature, and the mixture is stirred vigorously for 15 minutes. All volatile constituents are subsequently removed in vacuo, giving 4.98 g (yield: 98%) of a viscous liquid, which, according to $^{19}F$ NMR spectrum, consists of a 10:7 mixture of complexes (A) and (B).

NMR data (solvent: $CD_3CN$; reference substance: $^1H$, TMS; $^{19}F$, $CCl_3F$; $^{31}P$, 85% $H_3PO_4$):

Complex A $^1H$, δ, ppm=0.98 t (12H, 4CH$_3$), $^3J_{H,H}$=7 Hz; 1.36 m, (8H, 4CH$_2$); 1.61 m, (8H, 4CH$_2$); 2.02 d (3H, CH$_3$C(O)), $^4J_{H,P}$=1 Hz; 3.10 m, (8H, 4CH$_2$).

$^{19}F$, δ, ppm=−46.4 d, m (1F, PF$_2$), $^1J_{P,F}$=914 Hz; −79.7 d, m (1F, PF$_2$) $^1J_{P,F}$=862 Hz; −81.0 m (3F, CF$_3$); −82.6 m (6F, 2CF$_3$); −113.6 d, d (4F, 2CF$_2$), $^2J_{F(A),F(B)}$=292 Hz, $^2J_{P,F}$=104 Hz; −119.3 d, d (2F, CF$_2$), $^2J_{F(A),F(B)}$=292 Hz, 2J$_{P,F}$=90 Hz.

$^{31}P$, δ, ppm=−148.1 d, d,t,quin, $^1J_{P,F}$=914 Hz, $^1J_{P,F}$=862 Hz, $^2J_{P,F}$=104 Hz; $^2J_{P,F}$=90 Hz.

Complex B $^1H$, δ, ppm=0.98 t (12H, 4CH$_3$), $^3J_{H,H}$=7 Hz; 1.36 m, (8H, 4CH$_2$); 1.61 m, (8H, 4CH$_2$); 1.94 d (3H, CH$_3$C(O)), $^4J_{H,P}$=2 Hz; 3.10 m, (8H, 4CH$_2$).

$^{19}F$, δ, ppm=−62.0 d, m (2F, PF$_2$) $^1J_{P,F}$=826 Hz; −82.7 m (6F, 2CF$_3$); −83.1 m (3F, CF$_3$); −114.0 d, m (4F, 2CF$_2$), $^2J_{P,F}$=78 Hz; −114.8 d, m (2F, CF$_2$), 2J$_{P,F}$=78 Hz;

$^{31}P$, δ, ppm=−151.3 t, sept, J$_{P,F}$=826 Hz, $^2J_{P,F}$=78 Hz.

Example 35

Reaction with potassium oxalate, $K_2C_2O_4$, in acetonitrile

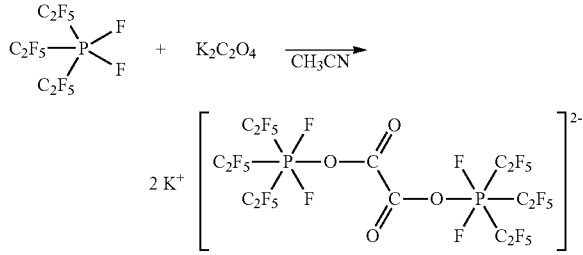

0.34 g (1.8 mmol) of potassium oxalate monohydrate (dried in an oil-pump vacuum at 140° C. for two hours) are suspended in 20 ml of acetonitrile, and 1.64 g (3.8 mmol) of tris(pentafluoroethyl)difluorophosphorane are added at room temperature. The reaction mixture is stirred vigorously for 1.5 hour in order to dissolve the oxalate. All volatile constituents are subsequently removed in vacuo, giving 1.88 g (yield: 100%, based on potassium oxalate employed) of a colourless solid.

NMR data (solvent: $CD_3CN$; reference substance: $^{19}F$, $CCl_3F$; $^{31}P$, 85% $H_3PO_4$):

$^{19}F$, δ, ppm=−60.3 d, m (2F, PF$_2$), $^1J_{P,F}$=836 Hz; −82.4 m (6F, 2CF$_3$); −83.1 m (3F, CF$_3$); −114--116 m (6F, CF$_2$).

$^{31}P$, δ, ppm=−148.8 t, sept, $^1J_{P,F}$=836 Hz; $^2J_{P,F}$=80 Hz.

IR Spectrum:

ṽ (CO)=1742.

The invention claimed is:

1. Compounds of the formula I

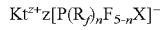    I, where R$_f$ in each case, independently of one another, denotes a straight-chain or branched fluoroalkyl group having 1 to 8 C atoms, X denotes OR, Ac, OAr or OHet, Ac denotes a carboxyl group OC(O)R, also including carboxyl groups of an aliphatic dicarboxylic acid resulting in compounds having the formula Ib

    Ib, where if z denotes 1 then x denotes 2 and y denotes 1, if z denotes 2 then x denotes 1 and y denotes 1, if z denotes 3 then x denotes 2 and y denotes 3, and if z denotes 4 then x denotes 1 and y denotes 2 and R' denotes a single bond or an alkylene group having 1 to 4 C atoms, Ar denotes an aryl group having 6 to 12 C atoms, which may be unsubstituted or substituted by Hal, NH$_2$, NAlk$_2$, NHAlk, NO$_2$, CN, SO$_3$H or OR, Alk denotes a straight-chain or branched alkyl group having 1 to 12 C atoms, Het denotes a heteroaryl group having 5 to 13 C atoms, which may be unsubstituted or substituted by Hal, NH$_2$, NAlk$_2$, NHAlk, NO$_2$, CN, SO$_3$H or OR, R denotes H, a straight-chain or branched alkyl group having 1 to 20 C atoms, which may be partially substituted by Hal, NH$_2$, NHAlk, NAlk$_2$, OH, NO$_2$, CN or SO$_3$H, or denotes a straight-chain or branched alkenyl group having 2 to 20 C atoms, which may contain a plurality of double bonds, where one or two non-adjacent carbon atoms of the alkyl or alkenyl group which are not bonded to the heteroatom may be replaced by atoms and/or atom groups selected from the group —O—, —S—, —S(O)—, —SO$_2$—, NH, —C(O)—, —O—C(O)— or —C(O)—O— and

Kt denotes a stabilized proton, a metal cation or an organic cation,

Hal denotes F, Cl, Br or I, z denotes 1, 2, 3 or 4, and n denotes 1, 2 or 3, and/or tautomers or stereoisomers thereof, including mixtures thereof in all ratios.

2. The compounds of claim 1, wherein Kt is a stabilised proton which is stabilized by an organic base or a basic solvent.

3. The compounds of claim 1, wherein Kt is a proton which is stabilized by an organic base, which is stabilised by an aromatic amine, a dialkylformamide or dialkylacetamide whose alkyl groups each have, independently of one another, 1 to 8 C atoms, as organic base.

4. The compounds of claim 1, wherein Kt is a proton which is stabilized by a basic solvent, wherein the basic solvent is selected from the group water, dialkyl ethers containing straight-chain or branched alkyl groups, which each have, independently of one another, 1 to 4 C atoms, aliphatic alcohols having 1 to 8 C atoms, ethyl acetate, acetonitrile, dimethyl sulfoxide or N-alkyl-2-pyrrolidone containing a straight-chain or branched alkyl group which has 1 to 8 C atoms.

5. The compounds of claim 1, wherein Kt is an organic cation selected from the organic cations of the formulae (1) to (8), ammonium cations of the formula (1), sulfonium cations of the formula (2) or oxonium cations of the formula (3))

    (1)

    (2)

or

    (3)

wherein

R$^0$ in each case, independently of one another, denotes

H, where all substituents R$^0$ in formula (2) cannot simultaneously be H, straight-chain or branched alkyl having 1-20 C atoms, straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms, or
aryl having 6 to 12 C atoms, which may be substituted by straight-chain or branched alkyl groups having 1-6 C atoms,
wherein $R^0$ may be partially substituted by halogen or partially substituted by —OR$^1$, —C(O)OR$^1$, —OC(O)R$^1$, —OC(O)OR$^1$, —C(O)NR$^1{}_2$ or —SO$_2$NR$^1{}_2$,
and wherein one or two non-adjacent carbon atoms of the radical $R^0$ which are not in the α-position may be replaced by atoms and/or atom groups selected from the group —O—, —S—, —S(O)—, —SO$_2$—, —N$^+$(R$^1$)$_2$—, —C(O)NR$^1$—, —SO$_2$NR$^1$— or —P(O)R$^1$—;
or
phosphonium cations of the formula (4)

[P(R$^2$)$_4$]$^+$ (4), wherein
$R^2$ in each case, independently of one another, denotes —N(R$^{1*}$)$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms, or
aryl having 6 to 12 C atoms, which may be substituted by straight-chain or branched alkyl groups having 1-6 C atoms,
wherein $R^2$ may be partially substituted by halogen or partially substituted by —OR$^1$, —C(O)OR$^1$, —OC(O)R$^1$, —OC(O)OR$^1$, —C(O)NR$^1{}_2$ or —SO$_2$NR$^1{}_2$,
and wherein one or two non-adjacent carbon atoms of the $R^2$ which are not in the α-position may be replaced by atoms and/or atom groups selected from the group —O—, —S—, —S(O)— or —SO$_2$—; or
uronium cations of the formula (5) or thiouronium cations of the formula (6)

[C(NR$^3$R$^4$)(OR$^5$)(NR$^6$R$^7$)]$^+$ (5)

or [C(NR$^3$R$^4$)(SR$^5$)(NR$^6$R$^7$)]$^+$ (6), wherein
$R^3$ to $R^7$ each, independently of one another, denote
H or N(R$^{1*}$)$_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms, or
aryl having 6 to 12 C atoms, which may be substituted by straight-chain or branched alkyl groups having 1-6 C atoms,
wherein one or more of the substituents $R^3$ to $R^7$ may be partially substituted by halogens or partially substituted by —OH, —OR$^1$, —CN, —C(O)NR$^1{}_2$, —SO$_2$NR$^1{}_2$, and where one or two non-adjacent carbon atoms of $R^3$ to $R^7$ which are not in the α-position may be replaced by atoms and/or atom groups selected from the group —O—, —S—, —S(O)—, —SO$_2$—, —N$^+$(R$^1$)$_2$—, —C(O)NR$^1$—, —SO$_2$NR$^1$—, or —P(O)R$^1$—; or
guanidinium cations of the formula (7)

[C(NR$^8$R$^9$)(NR$^{10}$R$^{11}$)(NR$^{12}$R$^{13}$)]$^+$ (7), wherein
$R^8$ to $R^{13}$ each, independently of one another, denote
H or N(R$^{1*}$)$_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated or partially unsaturated cycloalkyl having 3-7 C atoms, which may be substituted by straight-chain or branched alkyl groups having 1-6 C atoms, or
aryl having 6 to 12 C atoms, which may be substituted by straight-chain or branched alkyl groups having 1-6 C atoms,
wherein one or more of the substituents $R^8$ to $R^{13}$ may be partially substituted by halogens or by —OW, —CN, —C(O)NR$^1{}_2$, —SO$_2$NR$^1{}_2$,
and where one or two non-adjacent carbon atoms of $R^8$ to $R^{13}$ which are not in the α-position may be replaced by atoms and/or atom groups selected from the group —O—, —S—, —S(O)—, —SO$_2$—, —N$^+$(R$^1$)$_2$—, —C(O)NR$^1$—, —SO$_2$NR$^1$—, or —P(O)R$^1$—;
or
heterocyclic cations of the formula (8)

[HetN]$^+$ (8), wherein [HetN]$^+$ is a heterocyclic cation selected from the group comprising

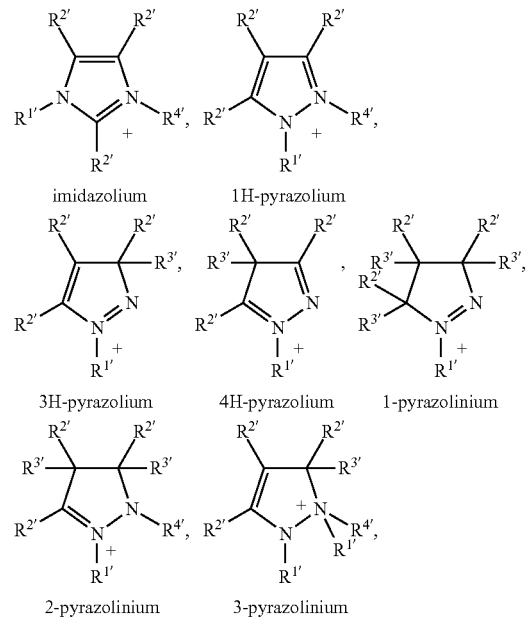

-continued

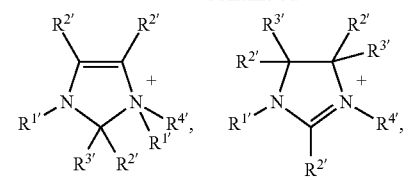
2,3-dihydroimidazolinium    4,5-dihydroimidazolinium

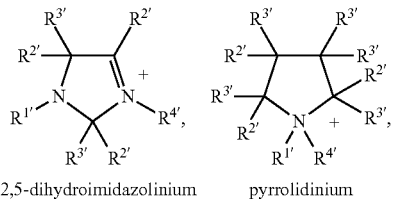
2,5-dihydroimidazolinium    pyrrolidinium

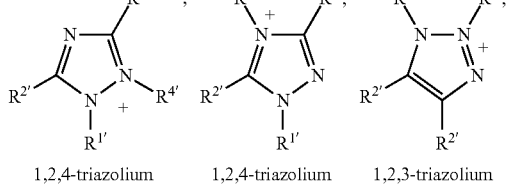
1,2,4-triazolium    1,2,4-triazolium    1,2,3-triazolium

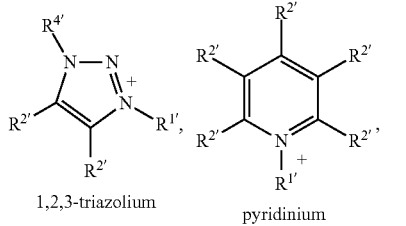
1,2,3-triazolium    pyridinium

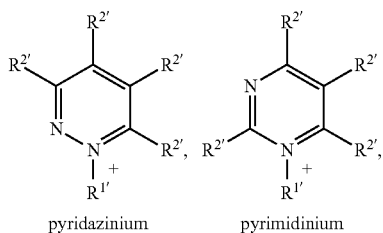
pyridazinium    pyrimidinium

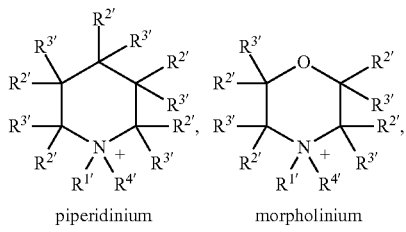
piperidinium    morpholinium

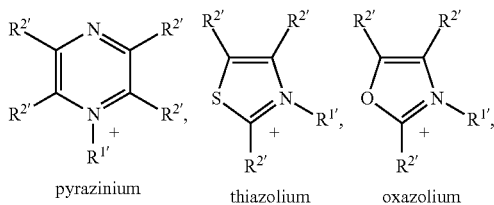
pyrazinium    thiazolium    oxazolium

-continued

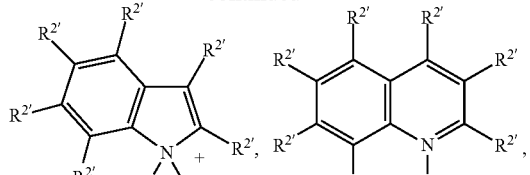
indolium    quinolinium

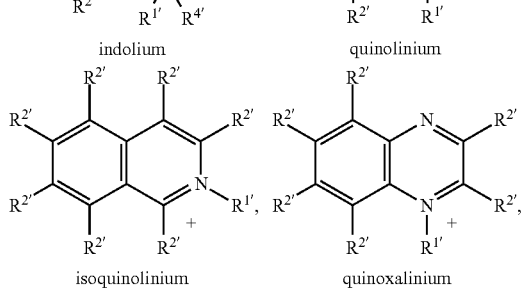
isoquinolinium    quinoxalinium

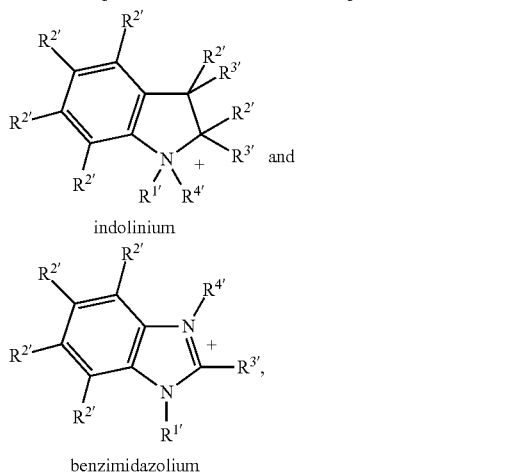
indolinium benzimidazolium wherein the substituents $R^{1'}$ to $R^{4'}$ each, independently of one another, denote

H, straight-chain or branched alkyl having 1-20 C atoms, which may also be fluorinated or perfluorinated, straight-chain or branched alkenyl having 2-20 C atoms and one or more double bonds, which may also be fluorinated or perfluorinated, straight-chain or branched alkynyl having 2-20 C atoms and one or more triple bonds, which may also be fluorinated, saturated or partially unsaturated cycloalkyl having 3-7 C atoms, which may be substituted by straight-chain or branched alkyl groups having 1-6 C atoms, aryl having 6 to 12 C atoms, which may be substituted by straight-chain or branched alkyl groups having 1-6 C atoms, or saturated, partially or fully unsaturated heteroaryl, heteroaryl-$C_1$-$C_6$-alkyl or aryl-$C_1$-$C_6$-alkyl, wherein the substituents $R^{1'}$, $R^{2'}$, $R^{3'}$ and/or $R^{4'}$ together may form a ring system, wherein one, two or three substituents $R^{1'}$ to $R^{4'}$ may be partially or fully substituted by halogens or partially by —$OR^1$, —CN, —C(O)$NR^1_2$, —$SO_2NR^1_2$, where the substituents $R^{1'}$ and $R^{4'}$ cannot be substituted simultaneously and fully by halogens, and wherein one or two non-adjacent carbon atoms of the substituents $R^{1'}$ to $R^{4'}$ which are not bonded to the heteroatom may be replaced by atoms and/or atom groups selected from the group consisting of —O—, —S—, —S(O)—, —SO$_2$—, —N$^+$(R$^1$)$_2$—, —C(O)NR$^1$—, —SO$_2$NR$^1$—, and —P(O)R$^1$—;

wherein R$^1$ stands for H, non- or partially fluorinated straight-chain or branched C$_1$- to C$_6$-alkyl, C$_3$- to C$_7$-cycloalkyl, unsubstituted or substituted phenyl and R$^{1*}$ stands for non- or partially fluorinated straight-chain or branched C$_1$- to C$_6$-alkyl, C$_3$- to C$_7$-cycloalkyl, unsubstituted or substituted phenyl.

6. The compounds of claim 1, wherein Kt is a metal cation selected from cations of the alkali metals, alkaline-earth metals, silver, copper, yttrium, ytterbium, lanthanum, scandium, cerium, neodymium, terbium, samarium, lanthanides, rhodium, rhutenium, iridium, palladium, platinum, osmium, cobalt, nickel, iron, chromium, molybdenum, tungsten, vanadium, titanium, zirconium, hafnium, thorium, uranium or gold, wherein the corresponding metal cations in solvated form or stabilised by ligands are also included.

7. Process for the preparation of compounds of the formula I according to claim 1, where Kt denotes a proton which is stabilised by an organic base, characterised in that a fluoroalkylfluorophosphorane of the formula II

   II, where R$_f$ in each case, independently of one another, denotes a straight-chain or branched fluoroalkyl group having 1 to 8 C atoms and n denotes 1, 2 or 3, is reacted with an organic base, where a compound of the formula IIIa, IIIb or IIIc arises

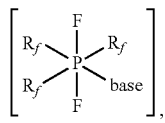   IIIa

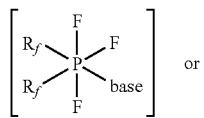   IIIb or

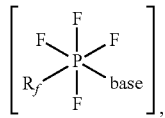   IIIc where R$_f$ in each case, independently of one another, has a meaning indicated above and the compound of the formula IIIa, IIIb or IIIc or a tautomeric or stereoisomeric form thereof is subsequently reacted with HX, where X denotes OR, Ac, OAr or OHet,
Ac denotes a carboxyl group OC(O)R,
Alk denotes a straight-chain or branched alkyl group having 1 to 12 C atoms,
Ar denotes an aryl group having 6 to 12 C atoms, which may be unsubstituted or substituted by Hal, NH$_2$, NAlk$_2$, NHAlk, NO$_2$, CN, SO$_3$H or OR,
Het denotes a heteroaryl group having 5 to 13 C atoms, which may be unsubstituted or substituted by Hal, NH$_2$, NAlk$_2$, NHAlk, NO$_2$, CN, SO$_3$H or OR,
R denotes H or an alkyl group having 1 to 20 C atoms, which may be partially substituted by Hal, NH$_2$, NHAlk, NAlk$_2$, NO$_2$, CN or SO$_3$H, or denotes an alkenyl group having 2 to 20 C atoms, which may contain a plurality of double bonds,
where one or two non-adjacent carbon atoms of the alkyl or alkenyl group which are not bonded to the heteroatom may be replaced by atoms and/or atom groups selected from the group —O—, —S—, —S(O)—, —SO$_2$—, NH, —C(O)—, —O—C(O)— or —C(O)—O—.

8. Process for the preparation of compounds of the formula I according to claim 1, where Kt denotes a metal cation or an organic cation, by a salt-exchange reaction, characterised in that a compound of the formula I, where Kt denotes a proton which is stabilised by a base, is reacted with a compound of the formula IV KtA   IV, where Kt denotes a metal cation or an organic cation, according to claim 1 or claim 3, 4 or 5 and
A denotes an anion selected from Cl$^-$, Br$^-$, I$^-$, OH$^-$, [R$_1$COO]$^-$, [R$_1$SO$_3$]$^-$, [R$_2$COO]$^-$, [R$_2$SO$_3$]$^-$, [R$_1$OSO$_3$]$^-$, [BF$_4$]$^-$, [SO$_4$]$^{2-}$, [HSO$_4$]$^{1-}$, [NO$_3$]$^-$, [(R$_2$)$_2$P(o)o]$^-$, [R$_2$P(O)O$_2$]$^{2-}$ or [CO$_3$]$^{2-}$, where R$_1$ in each case, independently of one another, denotes straight-chain or branched alkyl having 1 to 4 C atoms and R$_2$ in each case, independently of one another, denotes straight-chain or branched perfluorinated alkyl having 1 to 4 C atoms, where the electroneutrality of the salts of the formula KtA must be observed.

9. A method comprising performing a polymerization reaction or an isomerisation reaction which comprises employing a compound of claim 2 as an acid catalyst for said polymerization reaction or said isomerisation reaction.

10. A method of formulating a composition comprising adding a compound of the formula I according to claim 5 as a solvent or solvent additive, as a catalyst or phase-transfer catalyst, as conductive salt or as an electrolyte constituent, as a fluorosurfactant, as a heat-exchange medium, as a separating agent or extractant, as an antistatic, as a plasticiser, as a lubricant or constituent of lubricating oils or greases, as a hydraulic fluid or additive for hydraulic fluids, as a flame-proofing agent or as an additive in fire-extinguishing agents.

11. A method of formulating an electrolyte comprising adding a compound of the formula I according to claim 6 as catalyst or as additive in said electrolytes.

12. An electrolyte comprising at least one compound of the formula I according to claim 1.

13. An electrolyte according to claim 11, wherein the compound of the formula I is present in a molar concentration of 0.1 to 3.5 M.

14. An Electrochemical or opto-electronic cell containing at least one compound of the formula I according to claim 1.

15. Electrochemical or opto-electronic cell according to claim 14, wherein it is a photovoltaic cell, a light-emitting cell, an electrochromic or photoelectrochromic cell, an electrochemical sensor, a biosensor, a primary or secondary battery, a capacitor or a supercapacitor.

\* \* \* \* \*